US012702142B2

(12) United States Patent
Bhandari

(10) Patent No.: US 12,702,142 B2
(45) Date of Patent: Aug. 11, 2026

(54) BIOACTIVE DAIRY PRODUCTS AND PROCESSES FOR THEIR MANUFACTURE

(71) Applicant: Vivek Bhandari, Auckland (NZ)

(72) Inventor: Vivek Bhandari, Auckland (NZ)

( * ) Notice: Subject to any disclaimer, the term of this patent is extended or adjusted under 35 U.S.C. 154(b) by 121 days.

(21) Appl. No.: 17/942,023

(22) Filed: Sep. 9, 2022

(65) Prior Publication Data

US 2023/0014574 A1 Jan. 19, 2023

Related U.S. Application Data

(63) Continuation of application No. 16/640,305, filed as application No. PCT/NZ2018/050117 on Aug. 31, 2018, now abandoned.

(30) Foreign Application Priority Data

Sep. 4, 2017 (NZ) ....................................... 735194

(51) Int. Cl.

| | |
|---|---|
| ***A23B 11/12*** | (2025.01) |
| ***A23C 9/13*** | (2006.01) |
| ***A23C 9/152*** | (2006.01) |
| ***A23C 9/156*** | (2006.01) |
| ***A23C 9/16*** | (2006.01) |
| ***A23C 9/20*** | (2006.01) |
| ***A23G 9/38*** | (2006.01) |
| ***A23G 9/40*** | (2006.01) |
| ***A23G 9/42*** | (2006.01) |
| ***A23G 9/52*** | (2006.01) |
| ***A23L 2/38*** | (2021.01) |
| ***A23L 2/54*** | (2006.01) |
| ***A23L 33/19*** | (2016.01) |
| ***A61K 9/00*** | (2006.01) |
| ***A61K 35/20*** | (2006.01) |
| ***A61K 35/741*** | (2015.01) |

(52) U.S. Cl.

CPC ............ *A23C 9/1526* (2013.01); *A23B 11/12* (2025.01); *A23C 9/1307* (2013.01); *A23C 9/1315* (2013.01); *A23C 9/1528* (2013.01); *A23C 9/1565* (2013.01); *A23C 9/16* (2013.01); *A23C 9/206* (2013.01); *A23G 9/38* (2013.01); *A23G 9/40* (2013.01); *A23G 9/42* (2013.01); *A23G 9/52* (2013.01); *A23L 2/38* (2013.01); *A23L 2/382* (2013.01); *A23L 2/54* (2013.01); *A23L 33/19* (2016.08); *A61K 9/0056* (2013.01); *A61K 35/20* (2013.01); *A61K 35/741* (2013.01); *A23V 2002/00* (2013.01)

(58) Field of Classification Search

CPC ... A23C 9/1307; A23C 9/1315; A23C 9/1526; A23C 9/1528; A23C 9/16; A23C 9/206; A23C 3/02; A23C 7/04; A23G 9/38; A23G 9/40; A61K 35/20

See application file for complete search history.

(56) References Cited

U.S. PATENT DOCUMENTS

| | | | | |
|---|---|---|---|---|
| 8,062,687 | B2 | 11/2011 | Carroll et al. | |
| 2004/0028667 | A1 | 2/2004 | Norman et al. | |
| 2007/0207187 | A1 * | 9/2007 | Yajima .................. | A23C 21/08 424/234.1 |
| 2017/0000182 | A1 * | 1/2017 | Huber-Haag ........... | A23L 33/18 |

FOREIGN PATENT DOCUMENTS

| | | | |
|---|---|---|---|
| CN | 1557489 | A * | 12/2004 |
| CN | 101637201 | A | 2/2010 |
| CN | 106070639 | A | 11/2016 |
| CN | 106605705 | A | 5/2017 |
| CN | 106942378 | A * | 7/2017 |
| WO | 97/43905 | A1 | 11/1997 |

OTHER PUBLICATIONS

"Contents in Bovine Colostrum", 2020, Biodane-Pharma, https://web.archive.org/web/20200811151322/https://biodanepharma.info/contents-in-bovine-colostrum/ (Year: 2020).*

Deeth, H., "Uht processing of milk", 2012, New Food, https://www.newfoodmagazine.com/article/8203/uht-processing-of-milk/ (Year: 2012).*

Burling, H., Graverholt, G., "Milk—A new source for bioactive phospholipids for use in food formulations", 2008, Lipid Technology, vol. 20, No. 10, pp. 229-231 (Year: 2008).*

Translation of Yang_CN106942378A (Year: 2017).*

Translation of Gao_CN155749A (Year: 2004).*

Tran et al., "Hydrophilic lecithins protect milk proteins against heat-induced aggregation", 2007, Colloids and Surfaces B; Interfaces, 60, pp. 167-173 (Year: 2007).*

Gumus, C., "Utilization of Natural Emulsifiers and Their Derivatives to Formulate Emulsion-Based Delivery Systems for Hydrophobic Nutraceuticals", Doctoral Dissertations at University of Massachusetts Amherst, Jul. 2017, 6 pages.

Heneghan, C., "Why Demand for Aseptic Packaging is Increasing", Food Dive, [online], [retrieved Aug. 25, 2016], Retrieved from the Internet:<URL:https://www.fooddive.com/news/whydemand-for-aseptic-packaging-isincreasing/424854/#:~:text=The%20aseptic%20packaging%20process%20allows,the% 20retailer%20and%20consumer%20levels, 6 pages.

(Continued)

*Primary Examiner* — Kelly P Kershaw

(57) ABSTRACT

A process for the preparation of a liquid or semi-liquid bioactive dairy composition containing 20-90% retained bioactive IgG, for use as an ingredient in a ready-to-eat (RTE) or ready-to-drink (RTD) food product, includes the steps of a) combining a bioactive powder containing a colostrum powder and/or milk powder containing whey proteins, and immunoglobulin G (IgG), wherein the ratio of whey protein: IgG in the bioactive powder is between 1.74:1 and 3.05:1; water and a food grade acid to form a bioactive dairy composition with a pH of 2.5-4.0, and b) heat treating the bioactive dairy composition to between 67-145° C. at ambient pressure.

6 Claims, 11 Drawing Sheets

(56) References Cited

OTHER PUBLICATIONS

Hurley et al., "Perspectives on Immunoglobulins in Colostrum and Milk", 2011, Nutrients, vol. 3, 2011, pp. 442-474.

Li-Chan et al., "Stability of Bovine Immunoglobulins to Thermal Treatment and Processing", Food Research International, vol. 28, No. 1, 1995, pp. 9-16.

PCT International Search Report and Written Opinion, PCT International Application No. PCT/NZ2018/050117, dated Jan. 30, 2019, 5 pages.

PCT International Preliminary Report on Patentabilily, PCT International Application No. PCT/NZ2018/050117, dated Jul. 25, 2019, 6 pages.

* cited by examiner

Fig 1

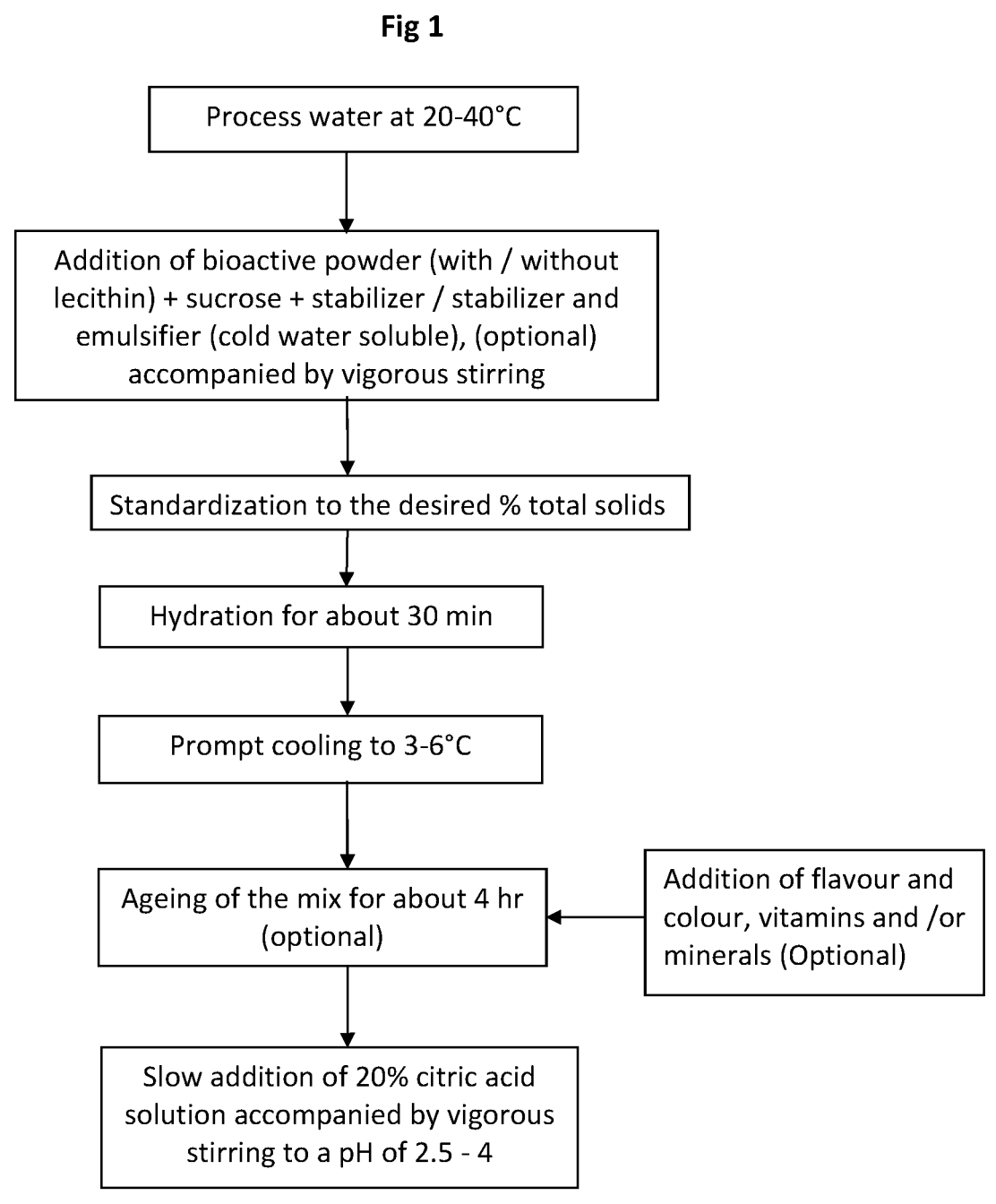

Process water at 20-40°C

Addition of bioactive powder (with / without lecithin) + sucrose + stabilizer / stabilizer and emulsifier (cold water soluble), (optional) accompanied by vigorous stirring Standardization to the desired % total solids Hydration for about 30 min Prompt cooling to 3-6°C Ageing of the mix for about 4 hr (optional)

Addition of flavour and colour, vitamins and /or minerals (Optional)

Slow addition of 20% citric acid solution accompanied by vigorous stirring to a pH of 2.5 - 4

BIOACTIVE DAIRY PRODUCTS AND PROCESSES FOR THEIR MANUFACTURE

FIELD OF INVENTION

This invention relates to bioactive dairy products and processes for their manufacture. More specifically, the invention relates to formulations and processes for the production of ready-to-eat or ready-to-drink dairy products containing bioactive immunoglobulin G (IgG).

BACKGROUND TO THE INVENTION

The proteins found in milk include immunoglobulins, growth factors, bovine serum albumin, (BSA), alpha lactalbumin, beta lactoglobulin and a large number of caseins and growth factors (IGF-Insulin-like Growth Factor and TGF-Transforming Growth Factor). However, the concentration of digestive enzymes, immunoglobulins, cytokines, interferons, growth factors, glycoproteins, proline-rich peptides and vitamins A, D, E and K are all higher in prime colostrum compared to standard milk.

Immunoglobulins (Igs), or antibodies, are a group of glycoproteins present in serum and tissue fluids of all mammals. There are five isotypes of Igs which all have a similar basic structure. The basic structure is a unit consisting of two identical light polypeptide chains and two identical heavy polypeptide chains linked together by disulphide bonds. The concentration of different Ig classes in colostrum and milk varies considerably according to species, breed, age, stage of lactation and health status and is often different from that in blood. For example, in human colostrum and milk, the IgA (Immunoglobulin A) class comprises about 90% and in blood 15-20% of total Igs whereas in cows the IgG (Immunoglobulin G) class is dominant in colostrum, milk and blood (about 80-90, 60-60 and 90% of total Igs, respectively).

In ruminants, e.g., cows, the absorption of Igs takes place during the first 12-36 hours after birth of the offspring. Ruminant neonates are born virtually without Igs and the colostral Igs are essential for survival. Bovine colostrum, which can be defined as milk from the first three milkings or milk collected during the first 24 hours after parturition, is rich in nutrients, antibodies and growth factors. According to another more common definition, colostrum is obtained during the first three days after calving. It contains three classes of immunoglobulins, IgG, commonly divided into two subclasses IgG1 (Immunoglobulin G1) and IgG2 (Immunoglobulin G2), IgA (Immunoglobulin A) and IgM (Immunoglobulin M). The main natural function of the colostrum immunoglobulins is to provide the new-born calf with passive immunity, mainly against bacterial and gastrointestinal infections by agglutination and stimulation of phagocytosis. A good colostrum has >60 mg immunoglobulins/ml corresponding to >30 mg IgGI/ml.

The relationship between human health and proper nutrition is now generally recognized and publications abound on this subject. Since the late 1970's much research has demonstrated the crucial role of the nutritional states of hospitalized patients. In the case of hospital patients, gastrointestinal infections, side effects of chemotherapy etc. may result in clinical symptoms of diarrhoea, inflammations, sepsis etc. Immune milk products can be used in the fight against hospital infections, one of health care's growing problems worldwide. These products offer a novel means for helping patients who cannot, or should not, be treated using current antibiotics (Maubois and Ollivier, 1997; Maubois, 1998;

Kelly and McDonagh, 2000). An intact and well-functioning intestinal tract is key to a faster recovery, reduction of complications etc. (Thompson, 1994; Spiller, 1997).

Dietary exposure to bovine IgG can have several effects on the human immune system. As any foreign protein bovine IgG may represent a potent antigen and stimulate production of antibodies. Both bovine IgG subclasses bind to human monocytes, but only bovine IgG1 bind to human B cells. This binding to human mononuclear cells may influence the human mucosal and systemic immune responses. IgG1 of bovine origin has been shown to protect against infection by various enteric pathogens in animal and in humans.

Efficacy of bovine milk colostrum or milk against microbial infections in humans is well documented. It is effective in the treatment of diarrhoea caused by *E. coli* and Rotavirus, gastritis caused by *Helicobacter pylori*, dysentery caused by *Shigella flexneri* and dental caries.

During processing, the stability of the Igs activity in colostrum or in milk is influenced by thermal treatments (Lindstrom et al., 1994; Li-Chan et al., 1995; Dominguez et al., 1997). High temperature/short time (HTST) pasteurization (72° C./15 sec) or batch pasteurization (63° C./30 min) results in only 0.5-10% loss of the Igs activity, whereas ultra-high temperature (UHT) treatment (138° C./4 sec) destroys the majority of the antibodies activity due to denaturation of Igs molecules.

The effect of processing on the stability of purified Igs or Ig concentrates derived from colostral whey (whey obtained from colostrum) has been the subject of many studies. Bovine IgG from colostral whey has been shown to be stable at neutral pH but with decreasing pH the stability is deteriorated (Chao-Cheng Chen et al. 1998).

U.S. Pat. No. 8,062,687 B2 relates to a method of pressure treating (pressure of 600 MPa/3 min) an acidified beverage prepared from colostral whey concentrate. The beverage prepared retained about 90% of the residual IgG.

The effect of heat on immunoglobulin in liquid whey has been investigated by Shimo et al (2015). When liquid whey from cow milk or colostrum is heated at pH 3.5-5.5 at 60-63° C., the IgG concentration is reduced by 2.67-21.64% whereas at 72° C./15 sec and 90° C./5 min reduced by 14.45-55.67%.

US Patent No. 2004/0028667A1 refers to a method of stabilising Igs in a solution having a pH below 4, wherein cereals or hydrolysed cereal products are added in an amount sufficient to prevent degradation. The invention also refers to a health drink or sports drink comprising immunoglobulins in a solution having a pH of 2.7-3.8, which are stabilised by the addition of cereals or hydrolysed cereal products.

In the dairy industry almost all studies on IgG are related to the heat stability of Igs present in whey derived from colostrum. This invariably involves the removal of casein, the principal protein of milk. Using known methods, utilization of such heat stable immunoglobulins in formulations, especially on a commercial scale would first require removal of casein, substantially increasing the processing cost for colostrum and also resulting in the loss of an important nutrient. It would be an advantage to obtain heat stable immunoglobulins with the casein, resulting in lower processing costs, as well as substantially improving the overall nutritional value of the formulated product.

U.S. Pat. No. 8,062,687 B2 describes a method of preparation of a beverage having high residual IgG but this is based on high pressure processing (HPP) technology which entails high cost of capital equipment which is not commercially viable, especially for small or medium scale manufacturers. Moreover, depending on the operating parameters and the scale of operation, the cost of high-pressure treatment is very high compared to the cost of thermal processing (Thakur and Nelson, 1998; Balasubramaniam, 2003).

There are many commercial products based on colostrum on the market. Most of these are used in the form of powder or tablets as nutritional food supplements for health-oriented consumers and sports enthusiasts. These do not have the same advantage as ready to drink products as for instance powders need to be reconstituted in water for domestic consumption. Moreover, these powders and tablets cannot be used in preparing products that have much longer shelf life under ambient conditions and greater consumer appeal, like UHT "Ready to drink" (RTD) acidified beverages with enhanced palatability, carbonated drinks, fermented dairy foods-UHT drinking yoghurt, set/stirred yoghurt, long life yoghurt, UHT juice milk drinks, drinking yoghurt with "live organisms", juice milk spreads/sauces, ice cream and related products, frozen yoghurt, desserts, flans, cheese, tea/coffee, etc.

The dairy and food industry would benefit immensely if products enriched with bioactive materials could be manufactured using thermal processing. Conventional thermal processing is low in capital cost and equipment and commercially more viable than other non-thermal technologies. Moreover, it will greatly benefit the consumer as the enriched products will be more affordable and yet provide a greater choice of highly nutritious and therapeutic products to the consumer.

OBJECT OF THE INVENTION

It is an object of the invention to provide a ready-to-eat or ready-to-drink food product including bioactive immunoglobulin.

Alternatively, it is an object to provide a bioactive dairy composition for use in the manufacture of food products containing bioactive immunoglobulins and a process for its manufacture.

Alternatively, it is an object to provide a process for the production of ready-to-eat or ready-to-drink food product including bioactive immunoglobulins.

Alternatively, it is an object of the invention to provide a bioactive dairy composition that may be incorporated into pharmaceutical, health or medicinal products.

Alternatively, it is an object of the invention to at least provide the public with a useful choice.

SUMMARY OF THE INVENTION

According to a first aspect of the invention there is provided a liquid or semi-liquid bioactive dairy composition, the composition formed from;

- a bioactive powder, the bioactive powder including a colostrum powder and/or milk powder, and Immunoglobulin G (IgG)
- water; and
- a food grade acid;

wherein the composition has a pH of between 2.5-4.0.

According to a further aspect of the invention there is provided a ready-to-eat (RTE) or ready-to-drink (RTD) food product including a heat-treated liquid or semi-liquid bioactive dairy composition having a pH of 2.5-4.0, the bioactive dairy composition including;

- a bioactive powder, the powder including a colostrum powder and/or milk powder, and immunoglobulin G (IgG), water and a food grade acid;

wherein the bioactive dairy composition has been heated-treated to 60-150° C.; and wherein the RTE or RTD food product including the bioactive dairy composition has a retained bioactive IgG level of 20-90% following heating.

More preferably, the liquid or semi-liquid bioactive dairy composition includes a sweetening agent.

Preferably, the composition has a pH between 3.2-3.9.

More preferably, the composition has a pH between 3.2-3.6.

Even more preferably the composition has a pH between 3.2-3.5.

Preferably the food grade acid is citric acid.

Preferably, the bioactive composition includes an emulsifier.

In preferred embodiments, the bioactive dairy composition further includes one or more ingredients selected from milk protein concentrate (MPC), whey powder, whey protein isolate, whey protein concentrate, sodium caseinate, calcium caseinate, lecithin, butter milk powder, beta serum powder, bovine serum IgG or IgG supplements.

More preferably, the one or more ingredients listed above are included in the bioactive powder.

Preferably, the bioactive dairy composition contains 1-45% by weight IgG.

More preferably, IgG in the bioactive dairy composition is obtained from the bioactive powder.

More preferably, the bioactive powder includes between 20-27% by weight IgG.

Preferably, the bioactive dairy composition includes 12-90% w/w protein.

More preferably, the protein in the composition is obtained from the bioactive powder.

More preferably, the bioactive powder includes 65-87% by weight protein.

Preferably, the bioactive dairy composition includes 0.08-10% w/w phospholipids.

Preferably, the bioactive powder used in the composition has 0.08%-10% by weight phospholipids (including lecithin, sphingolipids).

Preferably, the bioactive dairy composition includes 0.08%-9.5% by weight lecithin.

More preferably, the lecithin in the bioactive dairy composition is obtained from the bioactive powder.

Even more preferably, the bioactive powder contains 1.5%-2.0% by weight lecithin.

More preferably, lecithin may be derived from egg yolk, soy, sunflower, or from a milk source. The most preferred lecithin is soy or sunflower lecithin or derived from a milk source.

Preferably, the sweetening agent is selected from sucrose, glucose, honey, fructose, galactose, maltose, lactose, rhamnose, xylose, corn syrup solids, high fructose corn syrup solids (HFCS), maltodextrins, sorbitol, aspartame, acesulfame-K, saccharin, cyclamate, sucralose, stevia.

More preferably, the sweetening agent may be a liquid or semi-solid.

In further embodiments of the invention, the liquid or semi-liquid bioactive dairy composition includes one or more flavours, colours, vitamins and/or minerals.

In further preferred embodiments of the invention the bioactive dairy composition is a liquid, wherein the liquid composition includes 0.2-12% w/w bioactive powder.

More preferably, the liquid bioactive dairy composition includes 2-7% w/w bioactive dairy powder.

In alternative embodiments of the invention, the bioactive dairy composition is a semi-liquid wherein the semi-liquid composition includes 8-45% w/w bioactive powder. More preferably, the semi-liquid includes 9-25% w/w bioactive powder.

In further preferred embodiments, the bioactive dairy composition further includes 0.08-10% w/w phospholipids.

More preferably, the bioactive dairy composition further includes 0.08%-9.5% w/w lecithin.

In one embodiment of the invention, the bioactive dairy composition is a liquid "ready to drink" (RTD) beverage.

According to a further aspect of the invention, there is provided a ready-to-eat (RTE) or ready-to-drink (RTD) food product including bioactive immunoglobulins, the RTE or RTD food product produced using the liquid or semi-liquid bioactive dairy composition described above.

Preferably, the food product is an RTD product selected from acidified dairy beverages, UHT acidified dairy beverages, UHT drinking yoghurt, drinking yogurt with "live organisms", UHT juice milk drinks, carbonated drinks or a "prepared Beverage" like coffee, tea or hot chocolate.

More preferably, the RTD product is an acidified dairy beverage having 20-95% retained bioactive IgG.

Alternatively, the RTD product is a UHT drinking yoghurt having 20-90% retained bioactive IgG.

Alternatively, the RTD product is a UHT juice milk drink having 20-90% retained bioactive IgG.

Alternatively, the RTD product is a carbonated drink having 20-90% retained bioactive IgG.

In other preferred embodiments, the food product is an RTE product selected from set yoghurt, stirred yoghurt, frozen yoghurt, sorbet, sherbet, ice lolly, hard or soft ice cream, instant or frozen desserts, juice milk spreads, flans or hard and soft cheeses.

More preferably, the RTE product is a set yoghurt having 20-90% retained bioactive IgG.

Alternately, the RTE product is a stirred yoghurt having 20-90% retained bioactive IgG Alternatively, the RTE product is a frozen yoghurt having 20-85% retained bioactive IgG.

Alternatively, the RTE product is a sorbet or sherbet having 20-85% retained bioactive IgG.

According to a further aspect of the invention there is provided a process for the preparation of a liquid or semi-liquid bioactive dairy composition containing bioactive immunoglobulin G (IgG), the process including the steps of;

a) combining a bioactive powder containing a colostrum powder and/or milk powder, and IgG with a sweetening agent;

b) adding the bioactive powder and sweetening agent to water having a temperature of 20°-40° C. to form a mix and stirring;

c) following stirring, standardizing to required percent total solids with water;

d) hydrating for 25-35 minutes;

e) cooling the mix to 2-25° C.;

f) acidifying the mix by addition of a solution of food grade acid and stirring to achieve a pH of 3-4.

Preferably the cooling step at e) includes cooling the mix to 2-10° C.

Preferably the mix is aged following step e) for 3-5 hr after cooling.

Preferably 0.2-12% w/w bioactive powder is used at step a) to produce a liquid bioactive dairy composition.

More preferably, 2-7% w/w bioactive powder is used at step a).

Alternatively, 8-45% w/w bioactive powder is used at step a) to produce a semi-liquid composition.

Preferably, the food grade acid added at step f) is a 20% citric acid solution.

Preferably, the bioactive dairy composition is acidified at step f) to a pH of 3.2-3.9.

Preferably, the pH is adjusted at step f) to achieve a pH of 3.2-3.5.

Preferably, the process includes the further step of adding an emulsifier to the liquid or semi-liquid bioactive dairy composition.

In preferred embodiments, the process includes the further step of adding to the mix one or more ingredients selected from milk protein concentrate (MPC), whey powder, whey protein concentrate, sodium caseinate, calcium caseinate, lecithin, butter milk powder and beta serum powder.

Preferably the emulsifier added is lecithin, about 0.08%-9.5% by weight.

More preferably the bioactive dairy composition includes 0.08%-2% by weight lecithin.

More preferably, the lecithin in the bioactive dairy composition is obtained from the bioactive powder.

Preferably, the sweetening agent added in step b) is selected from one or more of sucrose, glucose, honey, fructose, galactose, maltose, lactose, rhamnose, xylose, corn syrup solids, high fructose corn syrup solids (HFCS), sorbitol, aspartame, acesulfame-K, saccharin, cyclamate, sucralose, stevia.

In some embodiments, the process includes the addition of one or more flavours, colours, vitamins and/or minerals to the mix.

In further embodiments there is provided a process for preparing an RTD beverage or RTE food product, the process including preparing a bioactive dairy composition according to the process described above, followed by the further steps of;

a) heating the bioactive composition to 60-150° C./1-1800 sec and b) cooling the composition to 2-25° C.

Preferably, the composition is heated to 60-102° C. over a period of 1-1800 seconds.

More preferably the composition is heated to 80-95° C./1-60 sec.

In further embodiments there is provided an acidified beverage formed using the process described above, wherein the bioactive dairy composition has a pH of 3.2-3.9, and wherein the acidified beverage has 20-95% retained bioactive IgG.

In other embodiments, a thickening or stabilising agent may be included, the thickening agent selected from locust bean gum, guar gum, xanthan gum, cassia gum, beta glucan, konjac flour, tara gum, gum arabic, gellan gum, carboxymehtylcellulose, microcrystalline cellulose, methylcellulose, tragacanth gum, karaya gum, gum acacia, chitosan, arabinoglactins, alginate, pectin, carrageenan, psyllium, or a mix thereof.

In some embodiments, emulsifiers other than lecithin may be selected from mono-diglycerides, acetic acid esters of monoglycerides, lactic acid esters of mono-diglycerides, citric acid esters of mono-diglycerides, diacetyl tartaric acid esters of monoglyceride, succinic acid esters of monoglycerides, ethoxylated mono-diglycerides, salts of fatty acids, polyglycerol esters of fatty acids, polyglycerol polyricinoleate, propylene glycol esters of fatty acids, sodium stearoyl lactylates, calcium stearoyl lactylates, sucrose esters of fatty acids, sorbates, polysorbates or a mix thereof.

A thickening or stabilising agent may be added alone or in combination with an emulsifier.

Preferably, the process for preparing the RTD beverage further includes the step of aseptically filling the beverage into packs for storage and sale.

Preferably, the RTD of RTE food product selected from an acidified dairy beverage, UHT acidified dairy beverage, UHT drinking yoghurt, UHT juice milk drink, acidified milk spread or carbonated drink has a shelf life at ambient temperature of up to 3-5 months when packed aseptically.

More preferably the RTE or RTD food product has retained IgG bioactivity of 70%-90% following 3-5 months of storage.

According to a still further aspect of the invention there is provided a process for the preparation of set yoghurt containing bioactive IgG, the process including;

a) heating a yoghurt mix at 85-95° C.;
b) cooling to 3-20° C.;
c) adding an amount of the bioactive dairy composition formed from the process described above to the yoghurt mix of b) and heating to 40-45° C.;
d) placing the yoghurt mix into containers for setting;
e) inoculating the yoghurt mix with a culture and fermenting to produce a yoghurt mix with pH 4-5; and
f) cooling the yoghurt.

Preferably, the bioactive dairy composition added at step c) contains 0.08-9.5% by weight lecithin.

More preferably the bioactive dairy composition includes 0.08-2% by weight lecithin.

Preferably, the pH at step e) is maintained at 4.4-4.5.

In further embodiments there is provided a set yoghurt formed using the process described above wherein the bioactive dairy composition has a pH of 3.2-3.9, and wherein the set yoghurt has 20-90% retained bioactive IgG.

According to a still further aspect of the invention there is provided a process for the preparation of stirred yoghurt containing bioactive IgG, the process including;

a) heating and homogenising a yoghurt mix at 85-95° C.;
b) cooling to 3-20° C.;
c) adding an amount of the bioactive dairy composition formed from the process described above to the yoghurt mix of b) and heating to 40-45° C.;
d) inoculating the yoghurt mix with a culture and fermenting to produce a coagulated product with pH 4-5;
e) breaking the coagulum formed in step d);
f) cooling the yoghurt mix of step d).

Preferably, the bioactive dairy composition added at step c) contains 0.08-9.5% by weight lecithin.

More preferably the bioactive dairy composition includes 0.08-2% by weight lecithin.

Preferably, the pH at step e) is maintained at 4.2-4.4.

In further embodiments there is provided a stirred yoghurt formed using the process described above wherein the bioactive dairy composition has a pH of 3.2-3.9, and wherein the stirred yoghurt has 20-90% retained bioactive IgG.

According to a further aspect of the invention there is provided a process for the preparation of a UHT RTD drinking yoghurt containing bioactive IgG, the process including;

a) providing a stirred yoghurt mix;
b) adding pectin and sweetening agent to the stirred yoghurt of step a);
c) adjusting the pH of the mix formed at step b) to 3.5-4.2;
d) heating the mix of step c) to 80-110° C.
e) homogenizing the heated mix of step d) at 150-200 bar pressure;
f) cooling the homogenized mix of e);
g) adding an amount of the bioactive dairy composition formed from the process described above to the cooled, homogenized mix of step f) followed by aseptic filling.

Preferably, the bioactive dairy composition added at step c) contains 0.08-9.50% by weight lecithin.

More preferably the bioactive dairy composition includes 0.08-2% by weight lecithin.

Preferably, the pH at step c) is maintained at 3.8-4.2.

Preferably, the process includes the optional addition of flavouring and/or fruit juice/juice concentrate following step b).

In further embodiments there is provided a UHT drinking yoghurt formed using the process described above wherein the bioactive dairy composition has a pH of 3.2-3.9, and wherein the UHT drinking yoghurt has 20-90% retained bioactive IgG.

According to a further aspect of the invention there is provided a process for the preparation of a UHT RTD dairy juice milk beverage containing bioactive IgG, the process including;

a) providing a juice or juice mix;
b) adding pectin and sweetening agent to the juice mix of step a);
c) adjusting the pH of the mix formed at step b) to 3.5-4.2;
d) heating the mix of step c) to 85-95° C.;
e) cooling the mix of step d);
f) adding an amount of the bioactive dairy composition formed from the process described above to the cooled mix of step e) followed by aseptic filling.

Preferably the process includes the optional addition of flavour and colour.

Preferably, the bioactive dairy composition added at step c) contains 0.08-9.5% by weight lecithin.

More preferably the bioactive dairy composition includes 0.08-2% by weight lecithin.

Preferably, the pH at step c) is maintained at 3.8-4.2.

In further embodiments there is provided a UHT juice milk beverage formed using the process described above wherein the bioactive dairy composition has a pH of 3.2-3.9, and wherein the UHT juice milk beverage has 20-90% retained bioactive IgG.

According to a further aspect of the invention there is provided a process for the preparation of a RTD carbonated dairy juice beverage containing bioactive IgG, the process including;

a) dissolving trisodium citrate and sodium benzoate in water and mixing;
b) adding a sugar syrup to the mix of step a);
c) adding a food acid solution to the mix of step b);
d) vigorously agitating the mix;
e) adding a juice concentrate, flavour and colour using a high shear agitator;
f) heating the mix of e) to 70-95° C. and subsequently cooling;
g) adding an amount of the bioactive dairy composition formed from the process described above to the mix of step f) followed by carbonation and filling.

Preferably the pH maintained at step e) is 2.5-4.

Preferably, the bioactive dairy composition added at step c) contains 0.08-9.5% by weight lecithin.

In further embodiments there is provided a carbonated dairy juice beverage formed using the process described above wherein the bioactive dairy composition has a pH of 3.2-3.9, and wherein the carbonated dairy juice beverage has 20-90% retained bioactive IgG.

More preferably the bioactive dairy composition includes 0.08-2% by weight lecithin.

According to a further aspect of the invention there is provided a process for the preparation of RTE frozen yoghurt containing bioactive IgG, the process including;

a) blending ice cream mix with a yoghurt mix;
b) adjusting or maintaining the pH of the mix of a) to 5.6-6.0;
c) ageing the mix for at least 60 minutes at less than 10° C.;
d) adding the bioactive dairy composition formed from the process described above to the mix in c);
e) freezing the mix of d) with incorporation of air to form a frozen yoghurt;
f) hardening the frozen yoghurt made in e).

Preferably the bioactive dairy composition added at step c) contains 0.08-9.5% lecithin.

More preferably the bioactive dairy composition includes 0.08-2% by weight lecithin.

In further embodiments there is provided a frozen yoghurt formed using the process described above wherein the bioactive dairy composition has a pH of 3.2-3.9, and wherein the frozen yoghurt has 20-85% retained bioactive IgG.

According to a further aspect of the invention there is provided a process for the preparation of a RTE sorbet containing bioactive IgG, the process including;

a) heating a sugar and stabilizer solution at 80-85° C.;
b) cooling the solution of step a) to 2-4° C.;
c) adding an amount of the bioactive dairy composition formed from the process described above to the mix of step b), together with fruit juice and/or fruit concentrate/citric acid/colour and flavour;
d) freezing the mix of c) with incorporation of air; and
e) hardening the product of d).

Preferably, the bioactive dairy composition added at step c) contains 0.08%-9.5% by weight lecithin.

More preferably the bioactive dairy composition includes 0.08-2% by weight lecithin.

In further embodiments there is provided an RTE sorbet formed using the process described above wherein the bioactive dairy composition has a pH of 3.2-3.9, and wherein the sorbet has 20-85% retained bioactive IgG.

According to a further aspect of the invention there is provided a process for the preparation of a RTE sherbet containing bioactive IgG, the process including;

a) heating a solution of sugar and a stabilizer to 80-85° C.;
b) cooling the solution of step a) to 2-4° C.;
c) adding an amount of ice cream to the cooled solution of b);
d) adding an amount of the bioactive dairy composition formed from the process described above to the mix of step c), together with fruit juice and/or fruit concentrate/citric acid, flavour and colour;
e) freezing the mix of d) with incorporation of air; and
f) hardening the product of e).

Preferably, the bioactive dairy composition added at step c) contains 0.08-9.5% by weight lecithin.

More preferably the bioactive dairy composition includes 0.08-2% by weight lecithin.

In further embodiments there is provided an RTE sherbet formed using the process described above wherein the bioactive dairy composition has a pH of 3.2-3.9, and wherein the sherbet has 20-85% retained bioactive IgG.

According to a further aspect of the invention there is provided an RTE dairy food product enriched with immunoglobulins, the RTE food product formed from ingredients including a reconstituted bioactive powder formed from a colostrum powder and/or milk powder, IgG and lecithin.

Preferably, the RTE dairy food product is a hard or soft ice cream, or instant dairy dessert. More preferably, the bioactive powder used in the preparation contains 2% lecithin.

Further aspects of the invention, which should be considered in all its novel aspects, will become apparent to those skilled in the art upon reading of the following description which provides at least one example of a practical application of the invention.

The present invention relates to formulations and methods for preparing ready to drink/fresh bioactive enriched dairy and related products using powders. Reference to a "bioactive" or "active" IgG is intended to mean that the protein is physiologically active when ingested and can have positive health benefits.

The terms "ready-to-eat" or "ready-to-drink" are intended to mean manufactured food products that can be consumed directly at purchase, without the need for any additional preparation steps, such as addition of water, heating, cooling or cooking for example.

BRIEF DESCRIPTION OF THE DRAWINGS

One or more embodiments of the invention will be described below by way of example only, and without intending to be limiting, with reference to the following drawings, in which:

FIG. 1 shows a flow chart for producing the bioactive dairy composition according to one embodiment of the invention;

DETAILED DESCRIPTION OF PREFERRED EMBODIMENTS OF THE INVENTION

Figure 2:
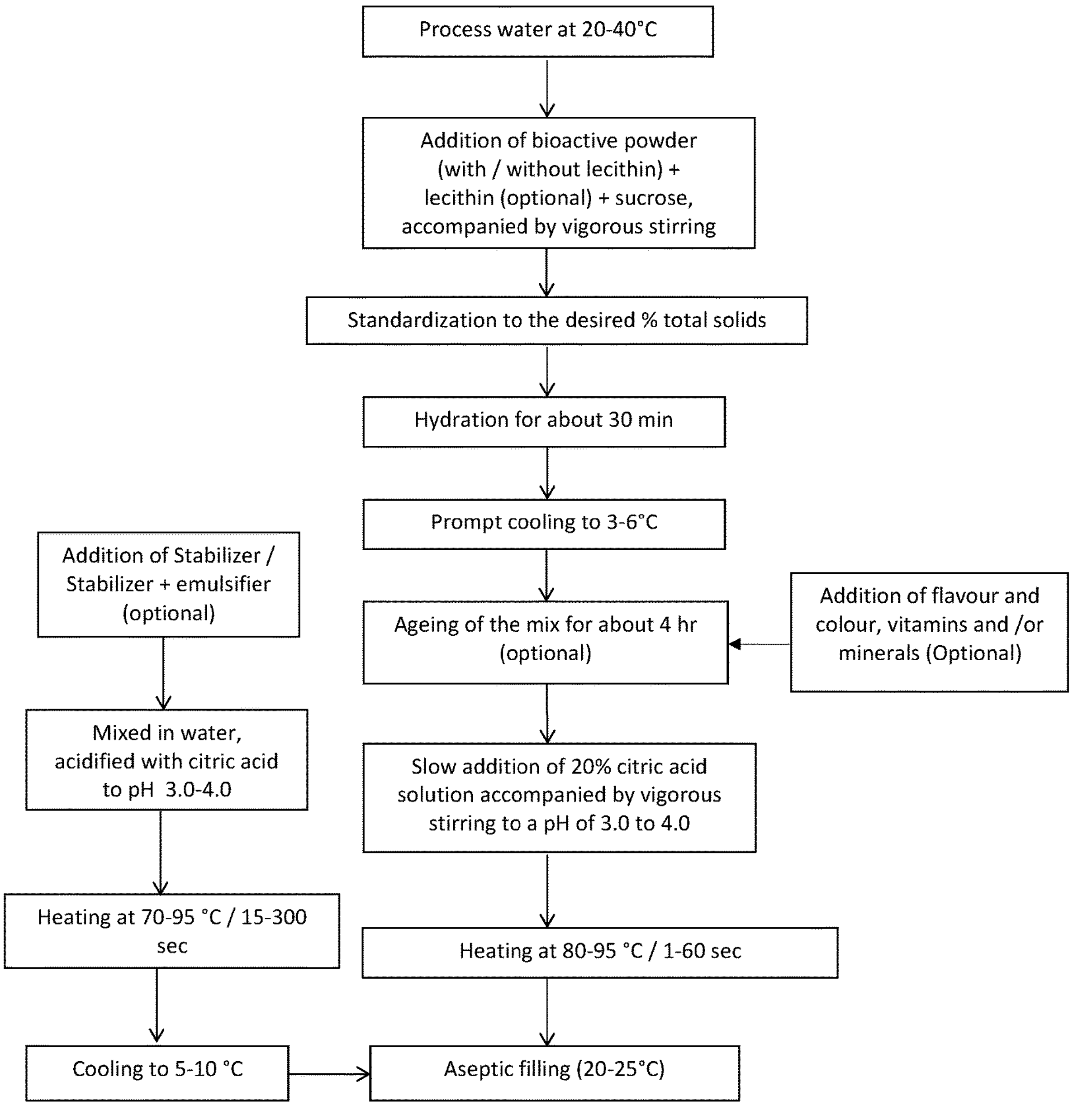
FIG. 2 shows a flow chart for producing a UHT dairy beverage containing active immunoglobulins according to one embodiment of the invention.

Dairy powders, especially spray dried colostrum powders are a rich source of immunoglobulins since a considerable amount of the antibody activity is retained after spray-drying at low temperatures. Colostrum powders offer the advantages of long shelf life under ambient conditions, uniformity of composition, convenience as these can be easily reconstituted and can be transported over long distances without any adverse effects on quality. These products can be blended with other dairy powders to get the desired composition of immunoglobulins, casein and whey proteins and reconstituted and processed to prepare different products having active IgG.

The present invention relates to formulations and methods for preparing "ready to drink" (RTD) and "ready to eat" (RTE) bioactive enriched dairy and dairy related products from dairy powders that retain bioactive immunoglobulin levels following processing.

A bioactive dairy composition with active IgG (un-denatured IgG) can be made from a bioactive powder which comprises colostrum powder and/or milk powder or a mix of colostrum powder, milk powder, milk protein concentrate (MPC)/whey protein concentrate (WPC), whey powder, bovine serum IgG, IgG supplements, lecithin, butter milk powder and beta serum powder. This bioactive dairy composition can be used as a base for the formulation of a wide range of RTE and RTD enriched dairy and dairy related products that retain active IgG in the final product.

Most of the commercially available bioactive powders may have IgG ranging from 18-50%, proteins ranging from 60-90%. Lecithin may be added to these powders during manufacture or it may be dry blended with powders. These powders may be used as a starting ingredient in the products of the present invention. Lecithin may be egg yolk lecithin, soy or sunflower lecithin or derived from a milk source. The preferred lecithin is soy or sunflower lecithin or derived from a milk source.

A wide range of bioactive powders may be made with differing ratios of ingredients, with the final composition of bioactive powder (particularly the total whey protein/IgG ratio, amount of casein and IgG present), used in the formation of the bioactive dairy composition being dependant on the required end food product.

A very important aspect of the invention relates to pH and its influence on the thermal stability of bioactive proteins like immunoglobulins. This pH is critically important in retaining the activity of bovine immunoglobulins in acidified or low pH products. These acidified products include (but not limited to) UHT acidified milk beverages, UHT juice milk drinks, carbonated drinks, fermented milks-UHT drinking yoghurt, set/stirred yoghurt, drinking yoghurt with live organisms, frozen yoghurt, sorbets and sherbets and related products, ice lolly, juice milk spreads/sauces, flans, cheese, etc.

A range of "Ready to Eat" (RTE) and "Ready to Drink" (RTD) products have been processed and their constituents before and after processing outlined in the examples below. The processes used can be seen in FIGS. 1-11.

When determining the amount of immunoglobulin G (IgG) in the final products, the AOAC Method Number: 2010.01, was used. This method determines the amount of active bovine IgG or native, i.e. non denatured and non-aggregated bovine IgG in bovine colostrum and bovine milk products and dietary supplements of bovine origin. Bovine caseins are removed during the sample preparation by precipitation at pH 4.6 as they may interfere with the assay. Therefore, the results for IgG are reported as "% IgG minus casein".

The term "retained bioactive IgG" used in relation to the final product should be taken to mean the amount of bioactive IgG retained in the final product after processing, relative to the amount of IgG initially present in the untreated product. The amount of bioactive IgG retained in a product depends on the composition and amount of the reconstituted bioactive dairy composition (made from bioactive powder) used in its production, the processing conditions employed in the production of reconstituted bioactive dairy composition-pH and the heat treatment.

FIG. 1 shows a process for the preparation of a bioactive dairy composition, the resulting composition being subsequently used in the formation of a range of products, including UHT acidified beverages, the preparation of which can be seen in FIG. 2 and FIG. 3.

The process shown in FIG. 1 optionally utilises dry sucrose. As would be clear to a person skilled in the art, should a liquid sweetening agent be used, the process will require the additional step of dissolving the bioactive powder (optionally along with lecithin) in water, before the addition of a liquid sweetening agent, followed by hydration (FIG. 3).

The active IgG levels in the bioactive dairy composition produced by the process of FIG. 1 are retained at substantially 100% throughout the process shown in FIG. 1, as this does not include a heating step, which can denature the IgG protein.

Figure 3:
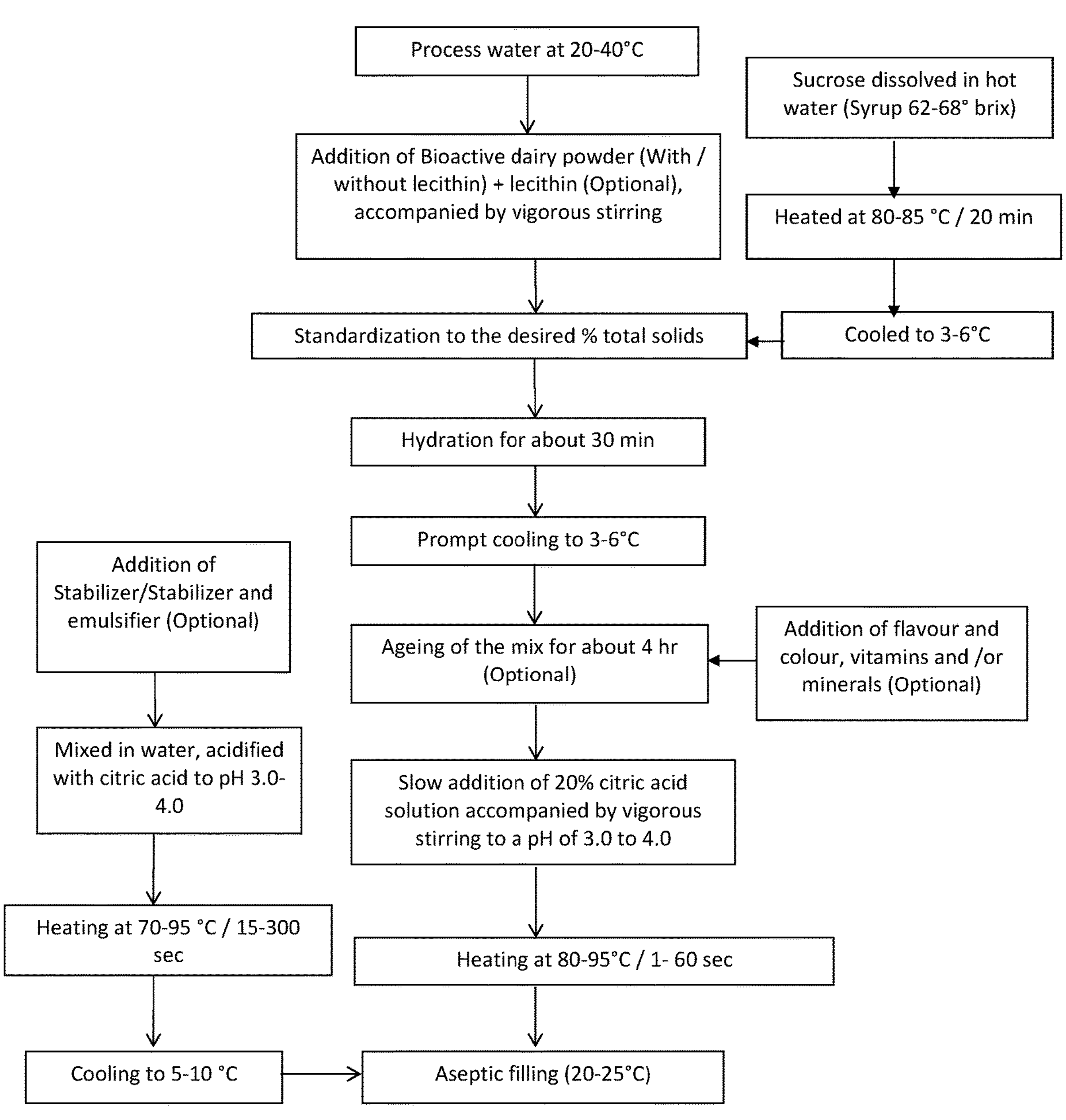
FIG. 3 shows a flow chart for producing a UHT dairy beverage having a liquid sweetening agent according to an alternative embodiment of the invention.

The bioactive dairy composition may also be consumed as a beverage without the additional steps described in the process of FIG. 2 and FIG. 3.

Referring to FIG. 2, the bioactive powder is blended with the required amount of sucrose and reconstituted in about 90% of the total amount of water at 20-40° C., while stirring the contents vigorously. The mix is standardized to the desired % total solids by adding remaining water, left undisturbed for hydration for about 30 min. It is then cooled to 3-6° C. and aged for 4 hr (ageing is optional). Optionally the required amount of flavour and colour, vitamins and/or minerals is added at this stage. The mix is acidified by slowly adding 20% citric acid solution, accompanied by vigorous agitation to a pH of 3.0-4.0.

The bioactive dairy composition is then heat treated at 80-95° C./1-60 sec. For industrial production and aseptic filling it should be cooled to 20 to 25° C. as shown in FIG. 2 and FIG. 3.

Besides sucrose any other sugar or sweetening agent may be used and may take any form such as a liquid or dry material. This may include (but not limited to) glucose, honey, fructose, galactose, maltose, lactose, rhamnose, xylose, corn syrup solids, high fructose corn syrup solids (HFCS), sorbitol, aspartame, acesulfame-K, saccharin, cyclamate, sucralose, stevia, etc. Besides citric acid, any food grade acid like lactic acid may be used.

If it is desired to thicken the product, a gum stabilizer may be selected from locust bean gum, guar gum, xanthan gum, cassia gum, beta glucan, konjac flour, tara gum, gum arabic, gellan gum, carboxymehtylcellulose, methylcellulose, microcrystalline cellulose (MCC), tragacanth gum, karaya gum, gum acacia, chitosan, arabinoglactins, alginate, pectin, carrageenan, psyllium, or a mix thereof. The stabilizer should preferably be added separately to the beverage as a solution after heat treatment and cooling.

Shelf life: UHT acidified beverages have a pleasant, refreshing taste. These include UHT acidified milk beverages, UHT drinking yoghurt, UHT juice milk drink, carbonated drinks and similar products. Since these products have relatively low pH, mostly ranging from 3.2-3.5, this provides a distinct advantage of being able to heat treat the products at relatively low temperatures which may range from 80-95° C., preserving the integrity of the native IgG proteins. Moreover, since powders generally have low bacterial counts, bioactive powders used in their preparation are also of good microbiological quality. When these products are heat treated and packed aseptically their shelf life ranges from 3-5 months under ambient conditions.

EXAMPLES

In all the examples related to acidified beverages and other products, the method of preparation of the bioactive dairy composition as outlined in FIG. 1 was followed. The bioactive dairy composition was incorporated into different products after heat treatment at 80-95° C./1-60 sec and cooling to 2-25° C.

In the examples that follow, reference to % retaining activity means % IgG activity retained (as compared to an untreated product) (control) after heat processing as determined by HPLC.

Example 1

Table 1 gives the composition of the bioactive powder used in the formation of the bioactive dairy composition, which may also be utilised directly as a beverage. In one composition (left column of the table) the IgG content is 20-21% in the bioactive powder. The ratio of whey proteins to IgG is approximately 3:1 by weight. The IgG activity retained in the bioactive dairy composition prepared therefrom (according to the process of FIG. 1) and heated at 86° C./30 sec is 45.8% at pH 3.1-3.3 while at pH 3.4-3.6 it is much lower, i.e. 29.2%.

In the other composition (right column of the table) the IgG content of the bioactive powder is 25-27% and the ratio of whey proteins to IgG is approximately 2:1. The IgG activity retained in the beverage prepared therefrom after heating under similar conditions is 37.2% at pH 3.1-3.3, while at pH 3.4-3.6 it is slightly higher, i.e. 41.0%. However, at neutral pH (6.4-6.6), under similar conditions of heat treatment, the IgG activity retained is 3.3%. This clearly shows that the IgG activity retained after processing is dependent on the composition of the bioactive powder and also more importantly on pH.

If it is desired to enhance mouth feel a hydrocolloid alone or in combination with an emulsifier may be added to the beverage. This is preferably added separately, i.e. after heat treatment and cooling to the heated and cooled bioactive dairy composition in order to obtain a higher activity of IgG. The IgG activity obtained with added guar gum before heating and when added separately is about 11% and 21% respectively at pH 3.4-3.6. A much lower activity obtained in the former case is plausibly due to an interaction on heating of a hydrocolloid (stabilising agent) with other beverage constituents like protein.

TABLE 1

UHT dairy beverage enriched with IgG

| Ingredients | % By weight | | Beverage heated with added guar gum (% w/w) | Guar gum added after heating (% w/w) | Ingredients | % By weight | | |
|---|---|---|---|---|---|---|---|---|
| Bioactive powder (Fat-1-3%, protein 80-87%, casein 20-22%, whey protein 60-65%, IgG 20-21%, bioactive IgG (minus casein) 15.7-16,3%, moisture 4-5%) | 4.5 | | | | Bioactive powder (Fat 0.2-2%, protein 79-85%, casein 32-34%, whey protein 47-51%, IgG 25-27%, IgG (minus casein) 15.6-19.2% moisture 4-5%) | 4.5 | | |
| Sucrose | 9-13 | | | | Sucrose | 9-13 | | |
| Citric acid, Water | qs | | | | Citric acid, Water | qs | | |
| Guar gum | | | 0.2 | 0.2 | Total | 100 | | |
| Total | 100 | | | | | | | |
| Chemical composition | % | | | | Chemical composition | % | | |
| Total solids | 14.2-18.2 | | | | Total solids | 14.2-18.2 | | |
| Milk fat | 0.07 | | | | Milk fat | 0.05 | | |
| Protein | 3.76 | | | | Protein | 3.69 | | |
| % IgG | 0.92 | | | | % IgG | 1.17 | | |
| % IgG (Minus casein) | 0.72 | 0.72 | 0.72 | 0.72 | % IgG (Minus casein) | 0.78 | 0.78 | 0.78 |
| pH | 3.1-33 | | 3.4-3.6 | | pH | 3.1-3.3 | 3.4-3.6 | 6.4-6.6 |
| IgG (Minus casein) | % | % | % | % | IgG (Minus casein) | % | % | % |
| % IgG (Contral) | 0.72 | 0.72 | 0.72 | 0.72 | % IgG (Central) | 0.78 | 0.78 | 0.78 |
| % IgG(Processed) | 0.33 | 0.21 | 0.08 | 0.15 | % IgG(Processed) | 0.29 | 0.32 | 0.026 |
| % Active IgG(Retained) | 45.8 | 29.2 | 11.1 | 20.8 | % Active IgG(Retained) | 37.2 | 41.0 | 3.3 |

Example 2

UHT Dairy Beverage Enriched with IgG and Lecithin

Another embodiment of the invention is related to the inclusion of lecithin in the bioactive powder at 0.5-8% by weight, preferably between 1.5-2.0%. Lecithin may be added to the bioactive powder before or after drying. It is preferred to add the lecithin before drying. If it is desired to enhance the lecithin content of the finished product, lecithin powder may be dry blended with the bioactive powder.

Alternatively, lecithin may also be added to the dairy beverage during processing (FIGS. 2 and 3). This may be soy or sunflower lecithin. The compositional details of the bioactive powder used and the bioactive dairy beverage made after heat processing at 84-92° C./15 sec are given in Table 2. The ratio of whey proteins to IgG is approximately 3:1 in the bioactive powder having 60-65% whey protein and 20-21% IgG. In the bioactive powder (4.5% by weight in the beverage) having 47-51% whey protein and 25-27% IgG, the ratio of whey protein to IgG is approximately 2:1. The bioactive powders contain 2% and 1.5-2% lecithin respectively. The differences in the activity of the IgG retained after processing of the beverage prepared are highly significant as compared to compositions without lecithin as is apparent from Tables 1 and 2.

At pH 3.2-3.3, 3.4-3.5 and 3.6-3.9 (Table 2), the IgG activity retained after processing (Bioactive powder is 4.5% by weight in the beverage) is 41.9%, 66.2 and 28.3% respectively when the ratio of whey proteins to IgG is approximately 3:1 by weight. Also, at 3.25% level and pH 3.4-3.5, the active IgG retained is about 81%. This shows the optimal pH for processing in this case is 3.4-3.5. When the bioactive dairy composition (4.5% by weight in the beverage) has a ratio of whey protein to IgG as approximately 2:1 by weight, the IgG activity retained is 88.5% and 42.3% at pH 3.2-3.3 and 3.4-3.5 respectively; the optimum pH in this case is 3.2-3.3.

However, at higher concentrations of bioactive powder (6.5% by weight) the IgG activity retained in the beverage is much lower, 39.8% at pH 3.2-3.3. Also, at pH 2.5, the IgG activity retained is 41.7%. This demonstrates that the IgG activity retained in the beverage is influenced by the composition of the bioactive powder; also, optimal pH and optimal concentrations of bioactive powder play a significant role in greatly enhancing IgG activity after processing.

The fact that lecithin affords significant protection to IgG against denaturation at low pH (pH 3.2-3.5) may be attributed to significant increase in the heat denaturation temperature of whey proteins thereby resulting in less aggregate formation in the presence of lecithin. Tran Le et al (2007) confirmed the effectiveness of lecithin as a hydrophobic agent for inhibiting aggregation of whey proteins. Though lecithin plays an important functional role in retaining the activity of Igs it also provides immense health benefits. Lecithin supports healthy brain function and nervous system. It has also shown positive effects in cognitive disorders, cardiovascular health, stress related disorders and memory. Sunflower lecithin is known to have a favourable phospholipid profile over lecithin from soybeans.

TABLE 2

UHT dairy beverage enriched with IgG and lecithin

| Ingredients | % by weight | Ingredients | % by weight | Ingredients | % by weight | | | |
|---|---|---|---|---|---|---|---|---|
| Bioactive powder (Milk fat 1-3%, protein 80-87%, casein 20-22%, whey protein 60-65%, IgG 20-21%, IgG (minus casein) 15.7-16.3% moisture 4-5%, lecithin 2%) | 4.5 | Bioactive powder (Milk fat 1-3%, protein 80-87%, casein 20-22%, whey protein 60-65%, IgG 20-21%, IgG (minus casein) 15.7-16.3%, moisture 4-5%) (No pre-added lecithin) | 3.25 | Bioactive powder (Milk fat - 0.2-2%, protein 79-85%, casein 32-34%, whey protein 47-51%, IgG 25-27%, IgG (minus casein) 15.6-19.2%, moisture 4-5%, lecithin 1.5-2%) | 4.3 | | 6.5 | 2.1 |
| Sucrose | 9-13 | | 8-12 | Sucrose | 9-13 | | 14-18 | 10-14 |
| Lecithin | | | 0.11 | | | | | 0.09 |
| Citric acid, water | qs | | qs | Citric acid, water | qs | | qs | qs |
| Total | 100 | | 100 | Total | 100 | | 100 | 100 |
| Chemical composition | | | | | | | | |
| Total solids | 14.19-18.19 | | 12.11-16.11 | | 14.19-18.19 | 14.19-18.19 | 2.1.40-25.40 | 13.59-17.59 |
| Milk fat | 0.09 | | 0.06 | | 0.05 | 0.05 | 0.07 | 0.02 |
| Protein | 3.76 | | 2.71 | | 3.69 | 3.69 | 5.33 | 1.72 |
| Lecithin | 0.09 | | 0.11 | | 0.08 | 0.08 | 0.11 | 0.13 |

TABLE 2-continued

| UHT dairy beverage enriched with IgG and lecithin | | | | | | | | | | |
|---|---|---|---|---|---|---|---|---|---|---|
| Ingredients | % by weight | | | Ingredients | % by weight | Ingredients | % by weight | | | |
| % IgG | 0.92 | | | | 0.66 | | 1.17 | 1.17 | 1.69 | 0.55 |
| % IgG (Minus casein) | 0.72 | 0.72 | 0.72 | | 0.52 | | 0.78 | 0.78 | 1.13 | 0.36 |
| pH | 3.2-3.3 | 3.4-3.5 | 3.6-3.9 | | 3.4-3.5 | | 3.1-3.3 | 3.4-3.6 | 3.1-3.3 | 2.4-2.5 |
| IgG (Minus casein) | | | | | | | | | | |
| % IgG (Control) | 0.72 | 0.72 | 0.72 | | 0.52 | | 0.78 | 0.78 | 1.13 | 0.36 |
| % IgG (Processed) | 0.31 | 0.49 | 0.21 | | 0.42 | | 0.69 | 0.33 | 0.45 | 0.15 |
| % Active IgG (Retained) | 41.9 | 66.2 | 28.3 | | 80.8 | | 88.5 | 42.30 | 39.8 | 41.7 |

Example 3

An acidified beverage having honey can be made from a bioactive powder. Incorporation of honey significantly enhances the nutritive and therapeutic value of the beverage as it is well known for its anti-inflammatory, antioxidant and immune-stimulatory activity. Any pure honey including but not limited to "Creamed honey" and "Manuka Honey" (Made in New Zealand) may be used.

A UHT beverage (heated at 87° C./15 sec) was made from bioactive powder having 1.5% lecithin with the sucrose in the formulation replaced partially with "Manuka" honey (A pure natural New Zealand honey) at 1% dosage and stevia at 0.016% in the formulation, according to the method outlined in FIG. 3. As shown in Table 3 it was possible to retain about 96% activity of IgG after processing at pH 3.2-3.3.

TABLE 3

| UHT dairy beverage having honey, enriched with IgG and lecithin | |
|---|---|
| Ingredients | % By weight |
| Bioactive powder (Fat 1.1%, Protein 85.02%, Casein34.52%, Whey Protein 50.5%, IgG 26.38%, IgG (Minus casein) 16.1%, Lecithin 1.5%, Moisture 4.88%) | 3.5 |
| Sucrose | 8.65 |
| Honey (Manuka) | 1 |
| *Stevia* | 0.016 |
| Citric acid, Water | qs |
| Lecithin | 0.05 |
| Total | 100 |
| Chemical composition | |
| Total solids | 12.84 |
| Milk fat | 0.04 |
| Protein | 2.98 |
| Lecithin | 0.12 |
| % IgG | 0.92 |
| % IgG (Minus casein) | 0.56 |
| pH | 3.2-3.3 |
| IgG (Minus casein) | % |
| % IgG (Control) | 0.56 |
| % IgG (Processed) | 0.54 |
| Active IgG (Retained) | 96.4 |

Example 4

Higher amounts of lecithin may be incorporated in an acidified beverage. The IgG activity retained in a processed beverage (heated at 87° C./15 sec) having pH 3.2-3.3 and about 0.3% lecithin is about 76% (Table 4-2$^{nd}$ column). Thus the nutritional value of the beverage can be further enhanced by adding more lecithin.

An acidified beverage (heated at 87° C./15 sec) may also be prepared from a bioactive powder having beta serum powder in addition to lecithin powder as one of the ingredients (Table 4-4th column). Although addition of beta serum somewhat reduces IgG activity, it provides additional health benefits as it is rich in milk fat globule membrane (MFGM) lipids and proteins. MFGM is a rich source of polar lipids like sphingolipids, phosphatidyl serine and phosphatidyl choline. Sphingolipids have an important role in neonatal gut maturation and suppression of gastrointestinal pathogens. Phosphatidyl serine restores normal memory on a variety of tasks while phosphatidyl choline supports liver recovery from toxic chemical attack or viral damage and promotes reduction of necrotising enterocolitis. Some of the MFGM proteins are Fatty acid binding protein (FABP), xanthine oxidase, mucin 1 and butyrophilin. FABP play an important role in the transport of fatty acids and regulation of lipid metabolism. Xanthine oxidase is a bactericidal agent while mucin1 provides protection against Rotavirus infection.

It can be seen clearly from the Examples 1 to 4 that a UHT acidified milk beverage enriched with IgG or IgG and lecithin and other valuable bioactive components can be made by low cost heat processing by having some unique formulations and optimal processing conditions. Furthermore, it demonstrates that it is possible to achieve IgG activity as high as 96%.

TABLE 4

| UHT dairy beverage enriched with IgG and lecithin/lecithin and MFGM | | | |
|---|---|---|---|
| Ingredients | % By weight | Ingredients | % By weight |
| Bioactive powder (Colostrum powder, lecithin powder) (Fat 2%, Protein 75.89%, | 4.6 | Bioactive powder (Colostrum powder, Beta serum powder, Lecithin powder (Fat | 3.5 |

TABLE 4-continued

| UHT dairy beverage enriched with IgG and lecithin/lecithin and MFGM | | | |
|---|---|---|---|
| Casein 30.82%, Whey Protein 45.07%, IgG 25.93%, IgG (Minus casein) 18%, Lecithin 6.82%, Moisture 4.6%) | | 3.6%, Protein 68.83%, Casein 28.61%, Whey Protein 39.49%, MFGM protein 0.73%, IgG 22.2%, IgG (Minus casein) 15.7%, Total phospholipid 8.13%, Lecithin 7.41%, Moisture 4.5%) | |
| Sucrose | 7 | Sucrose | 7 |
| Citric acid, Water | qs | Citric acid, Water | qs |
| Total | 100 | Total | 100 |
| Chemical composition | % | Chemical composition | % |
| Total solids | 12.29 | Total solids | 11.24 |
| Milkfat | 0.09 | Milk fat | 0.13 |
| Protein | 3.47 | Protein | |
| Lecithin | 0.31 | Total phospholipids | 0.28 |
| IgG | 1.19 | Lecithin | 0.26 |
| IgG (Minus casein) | 0.83 | MFGM (Milk Fat Globule Membrane) Proteins | 0.0025 |
| pH | 3.2-3.3 | IgG | 0.78 |
| | | IgG (Minus casein) | 0.55 |
| | | pH | 3.2-3.3 |
| IgG (Minus casein) | % | % IgG (Minus casein) | % |
| % IgG (Control) | 0.83 | % IgG (Control) | 0.55 |
| % IgG(Processed) | 0.63 | % IgG(Processed) | 0.33 |
| % Active IgG(Retained) | 75.9 | % Active IgG(Retained) | 60 |

As mentioned earlier, the shelf life of a UHT dairy beverage is 3-5 months under ambient conditions.

In one example where shelf life was tested, an acidified dairy beverage having 0.68% IgG (0.48% IgG (Minus casein) and 2.57% protein was heated at 87° C./15 sec and aseptically packed at 20-25° C.

This was stored under ambient conditions and samples were drawn periodically for shelf stability studies, the results of which are shown in Table 4A.

TABLE 4A

| Storage Stability of UHT Beverage at 20° C. | | | |
|---|---|---|---|
| | 0 day storage | 4 months | 7 months |
| Bioactive IgG (%) | 0.30 | 0.29 | 0.26 |
| pH | 3.35 | 3.28 | 3.21 |
| Conforms | <1 | <1 | <1 |
| APC | 30 | 50 | 25 |
| Y & M Count | <1 | <1 | <1 |

Table 4A demonstrates that pH remains almost unchanged during the entire storage period of over 3-5 months. The product has excellent microbiological stability with very low APC and complete absence of Coliform and Yeast and Mold Count during the entire storage period. The loss in bioactive IgG was approximately 4% and 13% after 4 months and 7 months storage under ambient conditions, i.e. the original bioactivity retained was about 96% and 87% respectively. It is expected that 70-90% of IgG activity remains in the products produced by the technology described following 3-5 months of storage.

Bioactive powders can also be beneficially applied to enrich other products with IgG and lecithin as shown in the following examples (Examples 5 to 12).

Example 5

Another embodiment of the invention relates to the incorporation of the IgG in set/stirred yoghurt. A typical example of set/stirred fruit yoghurt made by using bioactive dairy composition having lecithin is given in Table 5.

Figure 4:
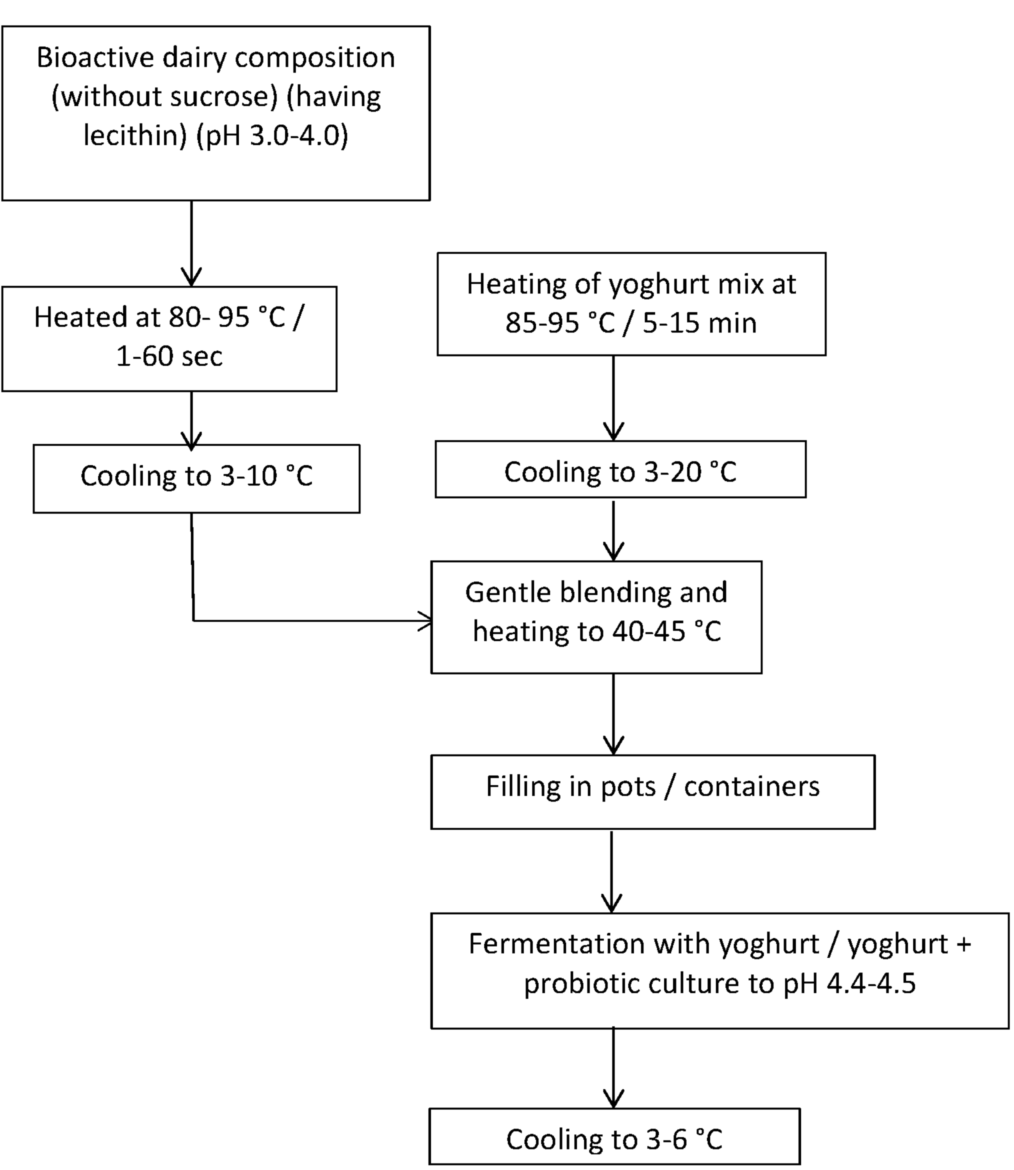
FIG. 4 shows a flow chart for producing a set yoghurt product containing active immunoglobulins in accordance with a further embodiment of the invention.

The method of preparation of set yoghurt is shown in FIG. 4 and involves standard procedure for the preparation of yoghurt mix and heating of bioactive dairy composition (formed by the process of FIG. 1), without the addition of the sweetening agent.

A) Preparation of Yoghurt Mix

Fresh skim or whole milk or reconstituted skim or whole milk is heated at 85 to 95° C. for 5 to 15 min (If whole milk is used, the milk is homogenized prior to heat treatment). It is then cooled promptly to a temperature of 3-20° C.

B) Preparation of Bioactive Dairy Composition

Bioactive powder is reconstituted in about 90% of the total amount of water (4.7 parts powder to about 85 parts water by weight) at 20-40° C. while stirring the contents vigorously. The reconstituted mix is standardized to the desired % total solids by adding remaining water, left undisturbed for hydration for about 30 min. It is then cooled to 3-6° C. and aged preferably for 4 hr (ageing is optional). It is acidified by slowly adding 20% citric acid solution (accompanied by vigorous agitation) to a pH of 3.2-3.3, heat treated at 87° C./15 sec and cooled to 3 to 10° C.

1 part of bioactive dairy composition as prepared above is added to 4 parts of the yoghurt mix by weight, taking care that the pH of the blend is not below pH 5.4 (the pH should be >pH 5.3, i.e. above the isoelectric point region of beta lactoglobulin to avoid whey separation) and the temperature of the finished mix brought to a fermentation temperature of 40-45° C. The finished mix is transferred into cups/containers and inoculated with the yoghurt/yoghurt+probiotic culture for 6-12 hr and incubated at 40-45° C. On reaching a pH of 4.4-4.5, the cups/containers are promptly transferred into a cold store for cooling at 3-6° C. There is a further drop in pH during storage. The pH of the finished product is generally 4.0 to 4.3.

Set yoghurt may also be prepared from a dry blend of instant whole milk powder and bioactive powder (Table 5) instead of the yoghurt mix prepared from fresh milk. The blend is reconstituted in water at 20-40° C. and hydrated for about 30 min. The procedure followed for fermentation of the mix is the same as described earlier for set yoghurt made from milk.

Figure 5:
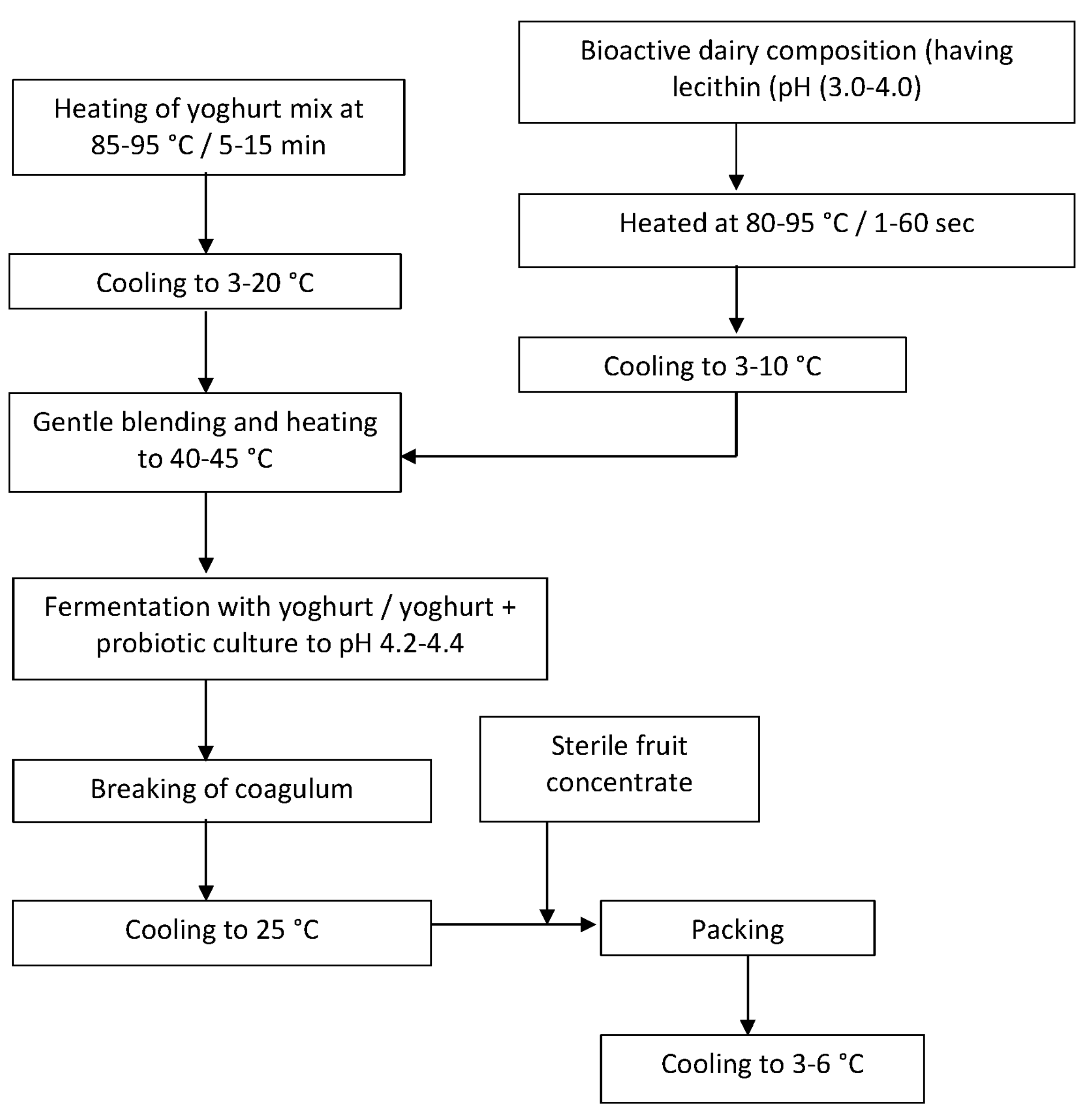
FIG. 5 shows a flow chart for producing a stirred yoghurt product containing active immunoglobulins in accordance with a further embodiment of the invention.

The procedure for stirred fruit yoghurt is the same as given for set yoghurt except that the finished mix is fermented to a pH of 4.2-4.4 and the coagulum stirred in such a way that it disintegrates all lumps and the curd obtained has a smooth surface. A flow chart outlining the steps for preparing a stirred fruit yoghurt is shown in FIG. 5. The product is cooled to about 25° C. and 5 to 15% of sterile fruit puree/concentrate is added and the finished product filled into cups/containers and then transferred into a cold store for cooling at 3-6° C. Since there is a further drop in pH during storage, the pH of the finished product is generally 4.0 to 4.3.

A variation to the above embodiment is the production of IgG enriched cheddar cheese which can be made by adding bioactive dairy composition to cooled milk which has been pasteurised (before inoculation with starter culture and addition of rennet) and ensuring that the pH of the mix is >5.4.

A further variation to the above embodiment is the production of IgG enriched cottage cheese which can be made by adding the bioactive dairy composition to the skim milk, before the addition of starter culture, taking care that the pH of the mix is >5.3.

TABLE 5

Set/stirred yoghurt enriched with IgG and lecithin

| Set/stirred Yoghurt | | Set/stirred Yoghurt made from powders | |
|---|---|---|---|
| Ingredients | % by weight | Ingredients | % by weight |
| Yoghurt mix composition | | Instant whole milk powder (Fat 26%, Protein 25%, Moisture 3.5%) | 8 |
| % Fat | 3.1 | Bioactive powder (Fat 1.1%, Protein 85.02%, Casein 34.52%, Whey protein 50.5%, IgG 26.38%, IgG (Minus casein) 16.1%, Lecithin 1.5%, Moisture 4.88%) | 2 |
| % Protein | 4.0 | Water | 90 |
| % Total solids | 14.7 | Total | 100 |

| | Bioactive dairy composition | % by weight | |
|---|---|---|---|
| | Bioactive powder (Fat 1.1%, Protein 85,02%, Casein 34.52%, Whey protein 50.5%, IgG 26.38%, IgG (Minus casein) 16.1%, Lecithin 1.5%, Moisture 4.88%) | 4.7 | |
| | Citric acid, water | qs | |
| | Total Chemical composition | 100 | |
| | % Fat | 0.05 | |
| | % Protein | 4.0 | |
| | % Total solids | 5.4 | |
| | % IgG | 1.24 | |
| | % IgG (Minus casein) | 0.76 | |
| | % Lecithin | 0.07 | |
| | pH (20° C.) | 3.2-33 | |
| | 1 part of bioactive dairy composition is blended with 4 parts of yoghurt mix by weight | | |

| Chemical composition of Finished Product | Set yoghurt | Chemical composition of finished product | Set yoghurt from powder |
|---|---|---|---|
| % Total Solids | 12.8 | % Fat | 2.1 |
| % Fat | 2.5 | % Protein | 3.7 |
| % Protein | 4.0 | % Total solids | 9.6 |
| % Lecithin | 0.01 | % Lecithin | 0.03 |
| % IgG (Control) | 0.25 | pH | 4.5 |
| pH | 4.3 | % IgG (Control) | 0.53 |
| IgG (Minus casein) | | IgG (Minus casein) | |
| % IgG (Control) | 0.15 | % IgG (Control) | 0.32 |
| % IgG (Finished Product) | 0.10-0.14 | % IgG (Finished Product) | 0.21-0.29 |
| % Active IgG (Retained) | 65 to 90 | % IgG (Retained) | 65 to 90 |

Example 6

Figure 6:
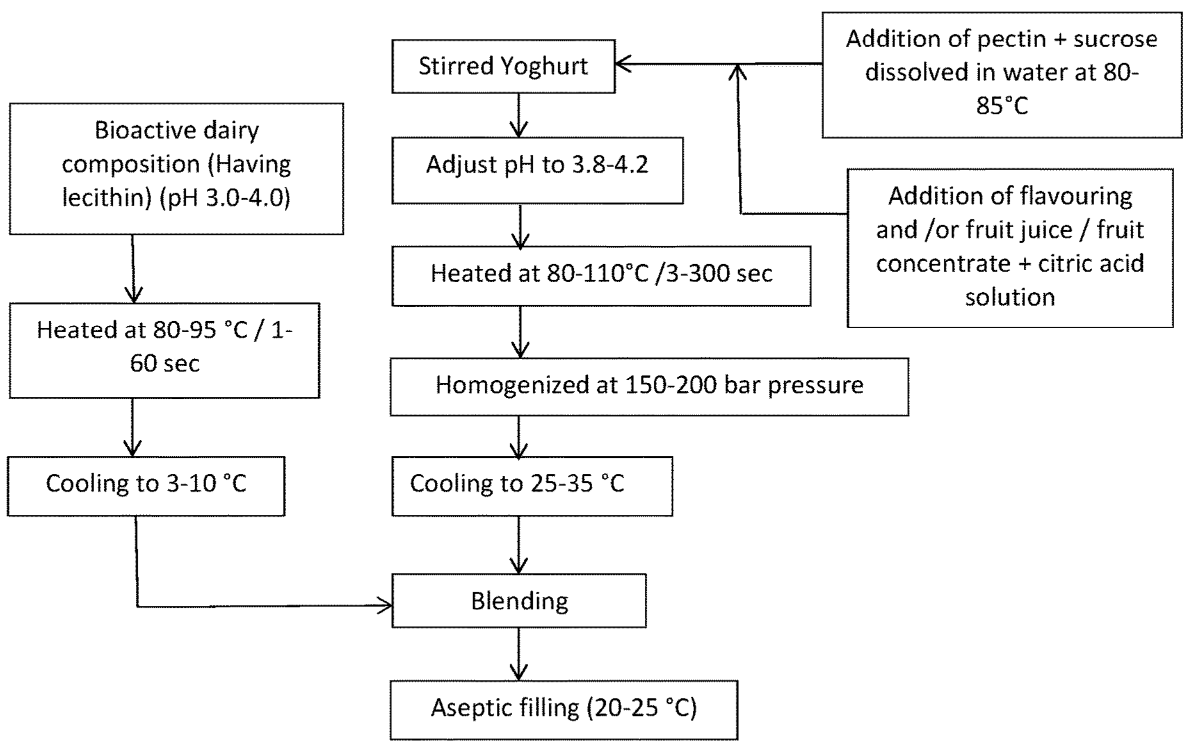
FIG. 6 shows a flow chart for producing UHT drinking yoghurt containing active immunoglobulins in accordance with a further embodiment of the invention.
Figure 7:
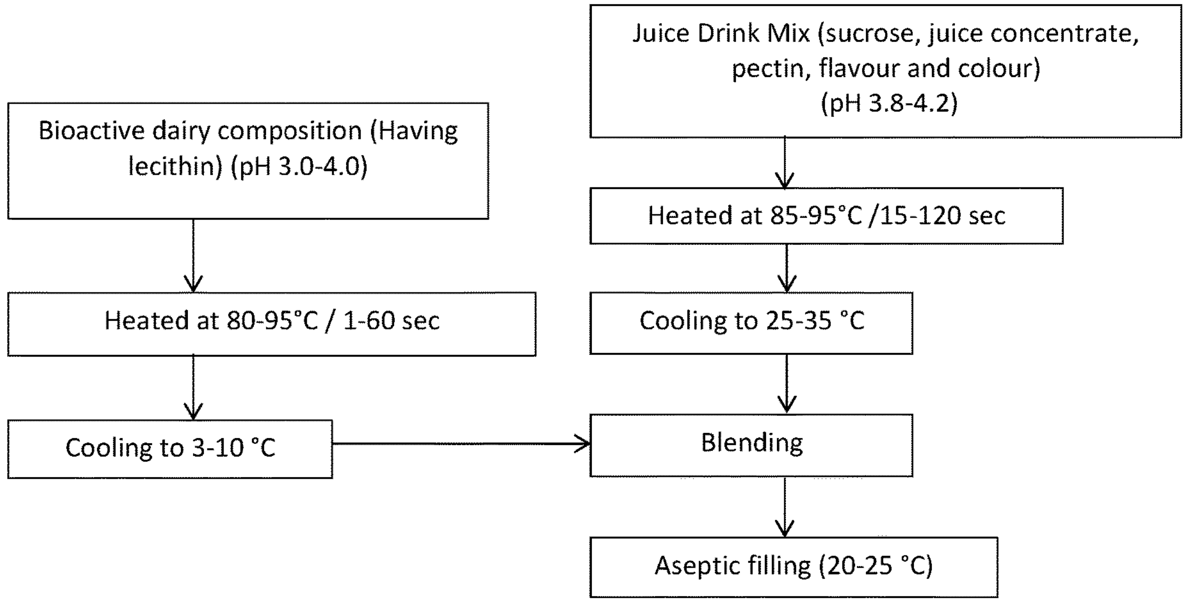
FIG. 7 shows a flow chart for producing UHT juice milk drink containing active immunoglobulins in accordance with a further embodiment of the invention.

UHT drinking yoghurt is made from stirred yoghurt (FIG. 6). The procedure for the preparation of UHT juice milk drink is given in FIG. 7.

An example of preparing an enriched drinking yoghurt/juice milk drink with IgG and lecithin is given in Table 6.

Method of Preparation

A) UHT Drinking Yoghurt

This involves preparation of stirred yoghurt by the standard procedure. Fresh skim or whole milk or reconstituted skim or whole milk is heated at 85 to 95° C. for 5 to 15 min (If whole milk is used, the milk is homogenized prior to heat treatment). It is then cooled promptly to a fermentation temperature of 40-45° C. and inoculated with a yoghurt/yoghurt+probiotic culture and fermented to a pH of 4.2-4.4 and the coagulum stirred in such a way that it disintegrates all lumps and the curd obtained has a smooth surface. It is then cooled to about 25° C.

The stabilizer generally used is pectin. Pectin is either dry blended with sugar (1:4 parts by weight) and added to water at 80-85° C., accompanied by vigorous agitation or dispersed in 10% saturated sugar solution at room temperature. This is followed by the addition of flavouring and/or fruit juice/fruit juice concentrate and the pH adjusted to 3.8-4.2 by adding citric acid solution. The yoghurt drink mix is pasteurised at 80-110° C./3-300 sec, homogenized at 150-200 bar pressure and cooled to 25-35° C.

B) UHT Juice Milk Drink

The procedure for the preparation of juice milk drink is the same as for drinking yoghurt except that no stirred yoghurt is added and homogenization is not necessary and the juice drink mix is heated at 85-95° C./15-120 sec and cooled to 25-35° C.

C) Preparation of Bioactive Dairy Composition

Bioactive powder is mixed with the required amount of sucrose and reconstituted in about 90% of the total amount of water (4 parts to 7 parts powder to about 79 to 66 parts water by weight) at 20-40° C. while stirring the contents vigorously. The reconstituted mix is standardized to the desired % total solids by adding remaining water, left undisturbed for hydration for about 30 min. It is cooled to 3-6° C. and aged preferably for 4 hr (ageing is optional). It is acidified by slowly adding 20% citric acid solution (accompanied by vigorous agitation) to a pH of 3.2 to 3.3, heat treated at 87° C./15 sec and cooled to 3 to 10° C.

Preparation of Finished Product: 1 part of bioactive dairy composition is added slowly to 2 parts of drinking yoghurt mix/juice drink mix by weight, accompanied by gentle stirring and filled aseptically at 20 to 25° C.

A variation to the above embodiment is a drinking yoghurt containing live organisms. In this variation, a pectin and sucrose solution is pasteurised, added to the stirred yoghurt and homogenized at 30-40° C. Pasteurised fruit juice is added to the mix, followed by blending with the pasteurised bioactive dairy composition and filling under hygienic conditions. The shelf life of this product is about 2-6 weeks under refrigeration.

TABLE 6

UHT drinking yoghurt/juice milk Drink enriched with IgG and lecithin

| Ingredients | Drinking Yoghurt mix % by weight | Juice Drink mix % by weight |
|---|---|---|
| Yoghurt mix (Having 4.2% protein, 0.12% fat, 11.5% total solids) | 30 | — |
| Sucrose | 6-8 | 6-8 |
| Stabilizer | 0.2-0.5 | 0.2-0.5 |
| Fruit Juice Concentrate (50° brix) and/or fruit flavour | 0.1-20 | 2-20 |
| Citric acid, water | qs | qs |
| Total | 100 | 100 |
| Chemical composition | | |
| % Fat | 0.0 | 0 |
| % Protein | 1.26 | 0 |
| % Total solids | 10.0-22.0 | 7.4-18.7 |
| pH (20° C.) | 3.8-4.0 | 3.2-3.6 |
| | Bioactive dairy composition % by weight | Bioactive dairy composition % by weight |
| Bioactive powder (Fat 1.5%, Protein 83%, Casein 33.65%, Whey protein 49.24%, IgG 26%, IgG (Minus casein) 16.2%, Lecithin, Lecithin 2%, Moisture 4.7%) | 4-7 | 4-7 |
| Sucrose | 7-18 | 7-18 |
| Citric acid, water | qs | qs |
| Total | 100 | 100 |
| Chemical composition | | |
| % Fat | 0.06-0.10 | 0.06-0.15 |
| % Protein | 3.32-5.81 | 3.32-5.81 |
| % Total solids | 11.7-25.87 | 11.7-25.87 |
| % IgG | 1-1.8 | 1-1.8 |
| % IgG (Minus casein) | 0.6-1.1 | 0.6-1.1 |
| % Lecithin | 0.08-0.14 | 0.08-0.14 |
| pH (20° C.) | 3.2-3.3 | 3.2-3.3 |
| 1 part of bioactive dairy composition is blended with 2 parts of drinking yoghurt/juice milk drink by weight | | |
| Chemical composition of Finished Product | | |
| % Total Solids | 9-25 | 8.83-21.09 |
| % Fat | 0.05-0.06 | 0.02-0.05 |
| % Protein | 1.95-2.78 | 1.11-1.94 |
| % Lecithin | 0.03-0.05 | 0.03-0.05 |
| % IgG control | 0.33-0.6 | 0.33-0.6 |
| IgG (Minus casein) | | |
| % IgG (Control) | 0.20 to 0.37 | 0.20 to 0.37 |
| % IgG (Finished Product) | 0.13-0.18 to 0.13-0.19 | 0.13-0.18 to 0.13-0.19 |
| % Active IgG (Retained) | 65-90 to 35-50 | 65-90 to 35-50 |

Example 7

Carbonated drinks have dissolved carbon dioxide which gives a sparkling and foaming effect when poured and consumed. In addition, carbon dioxide yields beverages with an extended shelf life.

A bioactive dairy composition (with/without heat treatment) (FIG. 1) may be carbonated or it may be blended with a carbonated drink.

An example of enriching carbonated drink with IgG and lecithin is given in Table 7.

Figure 8:
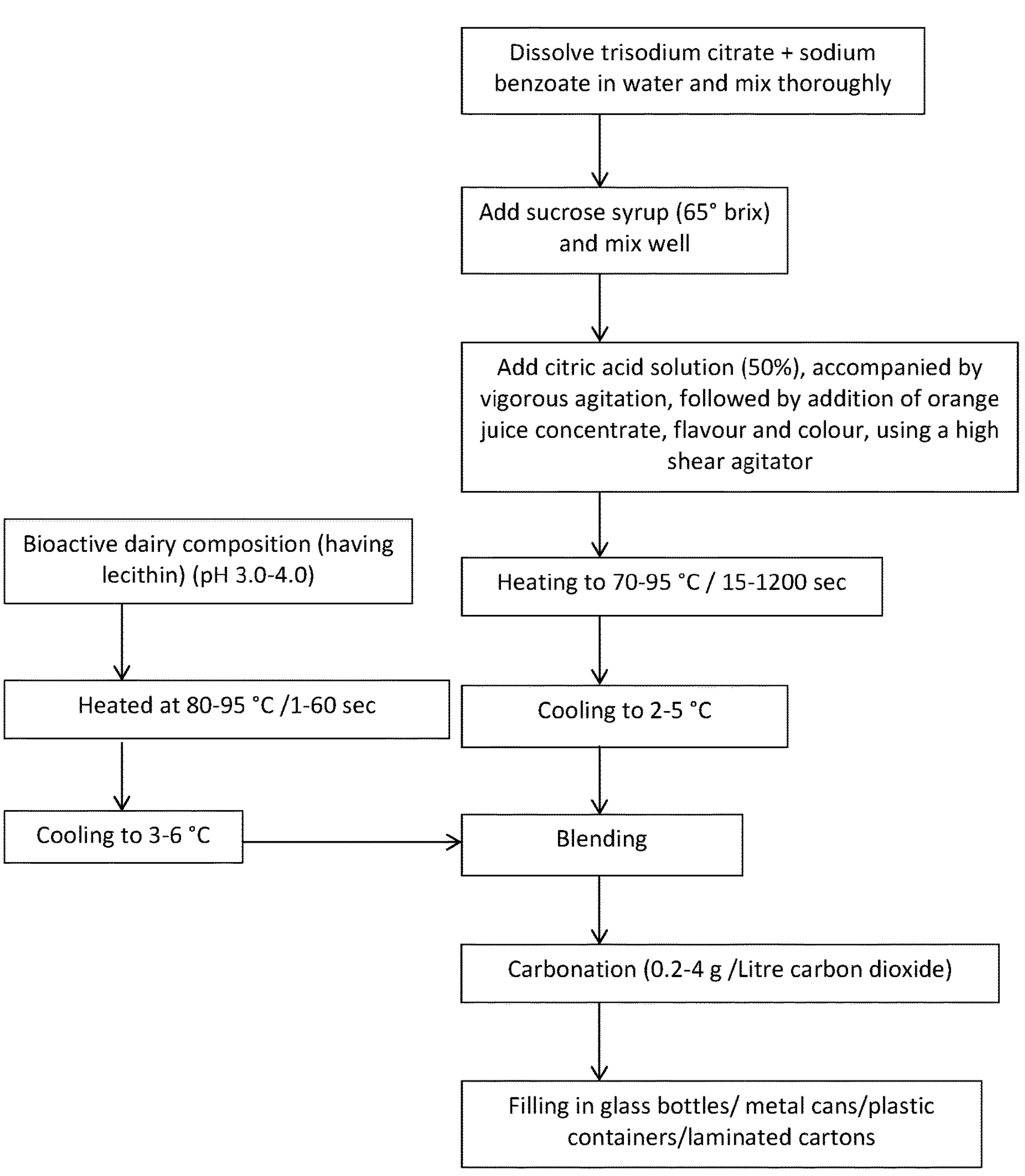
FIG. 8 shows a flow chart for producing carbonated juice milk drink containing active immunoglobulins in accordance with a further embodiment of the invention.

Method of Preparation (FIG. 8)

A) Bottling Syrup

1. Dissolve sodium citrate+sodium benzoate in water. Add sucrose syrup and mix thoroughly. Add citric acid (Preferably as 50% solution) slowly to the above solution, accompanied by vigorous agitation.

Add a premix of flavour and orange juice concentrate to the solution as prepared above, using a high shear agitator and add colour to the mix.

The pH of the juice drink is 3.1-3.6. It is heated at 70-95° C./15-1200 sec and cooled to 2-5° C.

B) Preparation of Bioactive Dairy Composition

Bioactive powder is blended with the required amount of sucrose and reconstituted in about 90% of the total amount of water (4 parts to 7 parts powder to about 79 to 66 parts water by weight) at 20-40° C. while stirring the contents vigorously. The reconstituted mix is standardized to the desired % total solids by adding remaining water, left undisturbed for hydration for about 30 min. It is then cooled to 3-6° C. and aged preferably for 4 hr (ageing is optional). The mix is acidified by slowly adding 20% citric acid solution (accompanied by vigorous agitation) to a pH of 3.2-3.3, heat treated at 87° C./15 sec and cooled to 3-6° C.

C) Preparation of Finished Product

The bottling syrup is combined with the bioactive dairy mix in the ratio of 1 part to 1 part by weight and carbonated and filled into glass bottles/metal cans/plastic containers/laminated cartons.

The amount of carbon dioxide in the finished product may range from 0.2 to 4 g/litre.

TABLE 7

| Carbonated drink enriched with IgG and lecithin | |
|---|---|
| Ingredients | % By Weight |
| Sucrose syrup (65 Brix) | 17 |
| Sodium benzoate | 0.02 |
| Trisodium citrate | |
| Orange juice concentrate (65 Brix) | 1.7 |
| Water, citric acid, colour, flavour | qs |
| Total | 100 |
| Analytical attributes | |
| Brix | 11.0 |
| pH (20° C.) | 3.1-3.6 |
| | Bioactive dairy composition % by weight |
| Bioactive powder (Fat 1.5%, Protein 83%, Casein 33.65%, Whey protein 49.24%, IgG 26%, IgG (Minus casein) 16.2%, Lecithin 2%, Moisture 4.7%) | 4-7 |
| Sugar | 7-18 |
| Citric acid, water | qs |
| Total | 100 |
| Chemical composition | |
| % Fat | 0.06-0.10 |
| % Protein | 3.32-5.81 |
| % Total solids | 11.7-25.87 |
| % IgG | 1-1.8 |
| % IgG (Minus casein) | 0.6-1.1 |
| % Lecithin | 0.08-0.14 |
| pH (20° C.) | 3.2-3.3 |
| 1 part of bioactive dairy composition is blended with 1 part of juice drink (Before carbonation) by weight | |
| Chemical composition of Finished Product | Carbonated Drink |
| % Total Solids | 11.3-18.43 |
| % Fat | 0.03-0.05 |
| % Protein | 1.66-2.9 |
| % Lecithin | 0.04-0.07 |
| % IgG (Control) | 0.5-0.9 |
| IgG (Minus casein) | |
| % IgG (Control) | 0.3 to 0.55 |
| % IgG (Finished Product) | 0.2-0.27 to 0.19-0.27 |
| % Active IgG (Retained) | 65-90 to 35-50 |

Example 8

For several years frozen yoghurt has been attracting the attention of consumers, especially in Europe and USA. Since yoghurt is known for its unique health and nutritional benefits, consumers associate frozen yoghurt with freshness and healthiness.

Frozen yoghurt with live bacteria is usually made with two separate mixes, i.e. an ice cream mix and a yoghurt mix consisting of plain yoghurt with live bacteria. Preparation of two separate mixes provides flexibility in producing frozen yoghurt with different levels of plain yoghurt. An example of enriching frozen yoghurt with IgG and lecithin is given in Table 8. The method of preparation is given below (FIG. 9):

A) Frozen Yoghurt Mix

Prepare ice cream base mix by mixing all the ingredients, followed by pasteurisation at 80-85° C./20-40 sec and homogenization at 80° C. using a homogenizing pressure of 220 bars. Cool to 5° C.

Prepare plain yoghurt mix by mixing all the ingredients, homogenize at 75° C., using a pressure of 150 bars and pasteurise at 95° C. for 5 min. It is then cooled to fermentation temperature of 40-45° C. and fermented with a yoghurt culture to a pH of 4.5 to 4.6, followed by prompt cooling to 5° C. Now mix 70 kg ice cream base mix with 30 kg plain yoghurt.

B) Preparation of Bioactive Dairy Composition

Bioactive powder is blended with the required amount of sucrose and reconstituted in about 90% of the total amount of water (5 parts powder to about 67 parts water by weight) at 20-40° C. while stirring the contents vigorously. The reconstituted mix is standardized to the desired % total solids by adding remaining water, left undisturbed for hydration for about 30 min. It is then cooled to 3-6° C. and aged preferably for 4 hr (ageing is optional). The mix is acidified by slowly adding 20% citric acid solution (accompanied by vigorous agitation) to a pH of 3.2 to 3.3, heat treated at 87° C./15 sec and cooled to 2-4° C.

C) Preparation of Finished Product

The frozen yoghurt mix is combined with the bioactive dairy mix in the ratio of 2 parts to 1 part by weight and aged for a period of 4 hr. The finished mix is frozen to an overrun (amount of air incorporated) of approximately 80%, hardened at −35 to −40° C. and stored at −18 to −23° C.

TABLE 8

Frozen yoghurt enriched with IgG and lecithin

| Ingredients | Ice cream base (%) | Yoghurt mix (%) | Finished Mix (%) |
|---|---|---|---|
| Fat | 2 | 2 | 2 |
| MSNF (Milk Solids Not Fat) | 12 | 10 | 11.4 |
| Sucrose | 17 | 0 | 11.9 |
| Dextrose | 3.5 | 0 | 2.45 |
| Corn syrup solids | 4.0 | 0 | 2.8 |
| Stabilizer-Emulsifier | 0.8 | 0 | 0.56 |
| Total Solids | 39.3 | 12 | 31.1 |
| pH (20 deg C.) | | | 5.6-5.0 |

| | Bioactive dairy composition % by weight |
|---|---|
| Bioactive powder (Fat 1.5%, Protein 83%, Casein 33.65%, Whey protein 49.24%, IgG 26%, IgG (Minus casein) 16.2%, Lecithin 2%, Moisture 4.7%) | 5 |
| Sucrose | 20 |
| Citric acid, water | qs |
| Total | 100 |
| Chemical composition | |
| % Fat | 0.07 |
| % Protein | 4.15 |
| % Total solids | 25.66 |
| % IgG | 1.3 |
| % IgG (Minus casein) | 0.81 |
| % Lecithin | 0.1 |
| pH (20° C.) | 3.2-3.3 |

1 part of the bioactive dairy composition is blended with 2 parts of the frozen yoghurt mix before freezing.

| Chemical composition of Finished Product | Frozen yoghurt |
|---|---|
| % Total Solids | 29.29 |
| % Fat | 1.35 |
| % Pratesn | 4.18 |
| % Lecithin | 0.03 |
| % IgG (Control) | 0.43 |
| IgG (Minus casein) | |
| % IgG (Control) | 0.27 |
| % IgG (Finished Product) | 0.16-0.19 |
| % Active IgG (Retained) | 60 to 85 |

Example 9

Sorbet is fruit ice with overrun and has a typical pH of 2.5 to 4.0. Sherbet is similar to sorbet except that it has some fat and milk solids not fat (msnf). Sorbet and sherbet have a refreshing taste and have become very popular in recent years.

An example of enriching sorbet/sherbet with IgG and lecithin is given in Table 9. The method of preparation is given below and with reference to FIG. 10 for the sorbet mix and FIG. 11 for the sherbet mix.

A) Sorbet/Sherbet Mix Preparation:

Water, sugar and glucose syrup are added to the mixing vat. The sugar solution is heated and the stabilizer dry mixed with sugar (1 part with 4 parts sugar by weight) is added and the mix pasteurised at a temperature of 80-85° C./20-40 sec and cooled to a temperature of 2-4° C. After cooling the desired quantities of fruit juice and/or fruit concentrate/flavour and colour and citric acid are added. The sherbet mix is prepared by adding 12 parts of standard ice cream mix to 88 parts by weight of the sorbet mix.

B) Preparation of Bioactive Dairy Composition

Bioactive powder is blended with the required amount of sucrose and reconstituted in about 90% of the total amount of water (5 parts powder to 74 parts water by weight) at 20-40° C. while stirring the contents vigorously. The reconstituted mix is standardized to the desired % total solids by adding remaining water, left undisturbed for hydration for about 30 min. It is cooled to 3-6° C. and aged preferably for 4 hr (ageing is optional). The mix is acidified by slowly adding 20% citric acid solution (accompanied by vigorous agitation) to a pH of 3.2-3.3, heat treated at 87° C./15 sec and cooled to 2-4° C.

C) Preparation of Finished Product

The sorbet/sherbet mix is blended with the bioactive dairy composition in the ratio of 1.5 parts to 1 part by weight. The finished mix is frozen (Overrun of 25-40% for sorbet and 35-45% for sherbet), followed by hardening at −35 to −40° C. and storage at −18 to −23° C.

A variation to the above embodiment is IgG enriched water ice which is similar to sorbet except that it is frozen in a quiescent state without any incorporation of air.

TABLE 9

Sorbet/Sherbet enriched with igG and lecithin

| Ingredients | Sorbet mix % by weight | Sherbet mix % by weight |
|---|---|---|
| Sucrose | 25 | 25 |
| Glucose syrup (75% solids) | 6 | 4 |
| Fruit concentrate (65° brix) | 7 | 7 |
| Stabilizer | 0.4 | 0.4 |
| Ice cream mix (12% fat, 11% MSNF (Milk solids not fat), 15% sucrose, 0.5% stabiliser/emulsifier) | 0 | 12 |
| Citric acid, water | qs | qs |
| Total | 100 | 100 |
| Composition | | |
| % Fat | 0 | 1.44 |
| % Protein | 0 | 0.48 |
| % Total solids | 34.65 | 37.77 |
| pH (20° C.) | 3.2-3.6 | 3.2-3.6 |

TABLE 9-continued

| Sorbet/Sherbet enriched with igG and lecithin | | |
|---|---|---|
| | Bioactive dairy composition % by weight | Bioactive dairy composition % by weight |
| Bioactive powder (Fat 1.5%, Protein 83%, Casein 33.65%, Whey protein 49.24%, IgG 26%, IgG (Minus casein 16.2%, Lecithin 2%, Moisture 4.7%) | 5 | 5 |
| Sucrose | 12 | 12 |
| Citric acid water | qs | qs |
| Total | 100 | 100 |
| Chemical composition | | |
| % Fat | 0.07 | 0.07 |
| % Protein | 4.15 | 4.15 |
| % Total solids | 17.66 | 17.66 |
| % IgG | 1.3 | 1.3 |
| % IgG (Minus casein) | 0.81 | 0.81 |
| % Lecithin | 0.1 | 0.1 |
| pH (20° C.) | 3.2-3.3 | 3.2-33 |
| 1 part of the bioactive dairy composition is blended with 1.5 parts of sorbet/sherbet mix by weight | | |
| Chemical composition of Finished Product | | |
| % Total Solids | 27.85 | 29.73 |
| % Fat | 0.02 | 0.9 |
| % Protein | 1.66 | 2.04 |
| % Lecithin | 0.04 | 0.04 |
| % IgG control | 0.52 | 0.52 |
| IgG (Minus casein) | | |
| % IgG (Control) | 0.32 | 0.32 |
| % IgG (Finished Product) | 0.19-0.27 | 0.19-0.27 |
| % Active IgG (Retained) | 60-85 | 60-85 |

Example 10

Ice cream powder can be conveniently reconstituted to meet the demand for hard ice cream and soft ice cream, especially during periods of low milk production in tropical countries. It can also be used by small scale manufacturers as they can avoid capital cost by not investing in a homogenizer and pasteuriser to prepare ice cream. Moreover, ice cream powder can be easily enriched with IgGs and thus provide passive immunity and also promote good gut health.

An example of ice cream enriched with IgG and lecithin is given below.

A) Soft Serve Ice Cream

A dry blend containing bioactive powder is reconstituted in water at 10-30° C. (Preferably 15-20° C.), accompanied by vigorous agitation. The reconstituted mix is hydrated for about 30 min. The mix is frozen on the soft serve machine and extruded at −6 to −7° C. and filled into cups or cones. The percent overrun may vary from 40 to 60 percent on the gravity machines to 60 to 100 percent on the pump machines.

B) Hard Ice Cream

Basically, the procedure for making hard ice cream is the same as given for soft serve ice cream except that the mix is frozen on a batch or continuous freezer, extruded at −4 to −5° C. and filled into cups, cones or other containers. After filling the product is hardened at −35 to −40° C. and subsequently stored at −18 to −23° C. before distribution.

Prepared beverages: A variation to the above embodiment is enrichment of "prepared beverages" like coffee, tea or hot chocolate with IgG. For example, a dry blend containing bioactive powder and buffering salts can be added to hot coffee. This formulation protects IgG against heat, even at temperatures >90° C. If necessary, a free-flowing agent may be added to the formulation.

Example 11

Gelled milk products of excellent quality can be made instantly by a "cold process". The cold process provides advantages of instant preparation and economy of pudding powders.

The method of preparation is given below:

A dry blend containing bioactive powder is reconstituted in water and the mix hydrated for about 30 min. Cold milk is added to the reconstituted mix. A dry pudding base containing a sweetening agent, buffering salts and a stabilizer is added to the reconstituted mix. The contents are poured into containers and refrigerated for 10-15 min. Pudding is "ready to serve".

A variation to the above embodiment is IgG enriched flan which can be made by using appropriate stabilizers, and in the case of acidified flan, a stabilizer, a suitable acidifying agent and emulsifying salts.

Example 12

The use of a semi-liquid bioactive dairy composition is exemplified here in the preparation of a acidified milk spread.

In the preparation of acidified milk spread 10-15 parts of bioactive powder is blended with 15 parts sugar by weight and added to water, at 20-30° C. The mixture is left undisturbed for hydration for approximately 30 min. The mix is cooled to 5-10° C. and flavour, colour and juice are added.

The pH of the mix is adjusted to 3.2-3.8 by adding slowly 20% citric acid, accompanied by vigorous stirring to create a semi-liquid bioactive dairy composition.

The semi-liquid bioactive dairy composition is then heated to a temperature of 80-85° C. for 1-3 min and cooled to 5-10° C.

A solution of stabilizer (previously heated to 85-90° C. and cooled to 5-10° C.) is added slowly to the above composition, accompanied by vigorous stirring, in order to obtain a uniform, homogeneous product. Optionally the product may be homogenized at very low temperature and pressure.

The process described for the preparation of the bioactive dairy composition and UHT acidified beverages (examples 1 to 4) is a preferred method (as shown in FIGS. 1, 2 and 3) since it avoids interaction of immunoglobulin G (IgG) present in the bioactive dairy composition with the stabilizer that may be added "optionally" to thicken the product. A further method is to add the stabilizer along with the bioactive dairy composition, but this may result in lower activity of IgG due to possible interaction of IgG with stabilizers (as observed from experimental data).

Also, the addition of a bioactive dairy composition to yoghurt mix directly in set/stirred yoghurt using known methods would result in a lower activity of IgG, due to possible interactions of IgG with yoghurt mix at high temperatures (85 to 95° C.) and higher pH (6.4-6.6). In the preferred method developed herein (example 5—FIGS. 4 and 5) the bioactive dairy composition is added separately, i.e. after cooling to 3 to 10° C., to yoghurt mix that has been cooled to 3-20° C. and subsequently heated gently to fermentation temperature of 40 to 45° C. to preserve IgG activity.

Similarly, in example 6 (UHT drinking yoghurt/juice milk drink) the preferred method of addition of bioactive dairy composition is to add it separately as shown in the flow chart (FIGS. 6 and 7) to avoid possible interaction of IgG with the stabilizer pectin at pH 3.8-4.2 at 80-110° C./3-300 sec.

In carbonated drinks also, the bioactive dairy composition should be added separately as shown in FIG. 8 in order to avoid possible interaction of IgG present in the bioactive dairy composition with the orange juice constituents.

Figure 9:
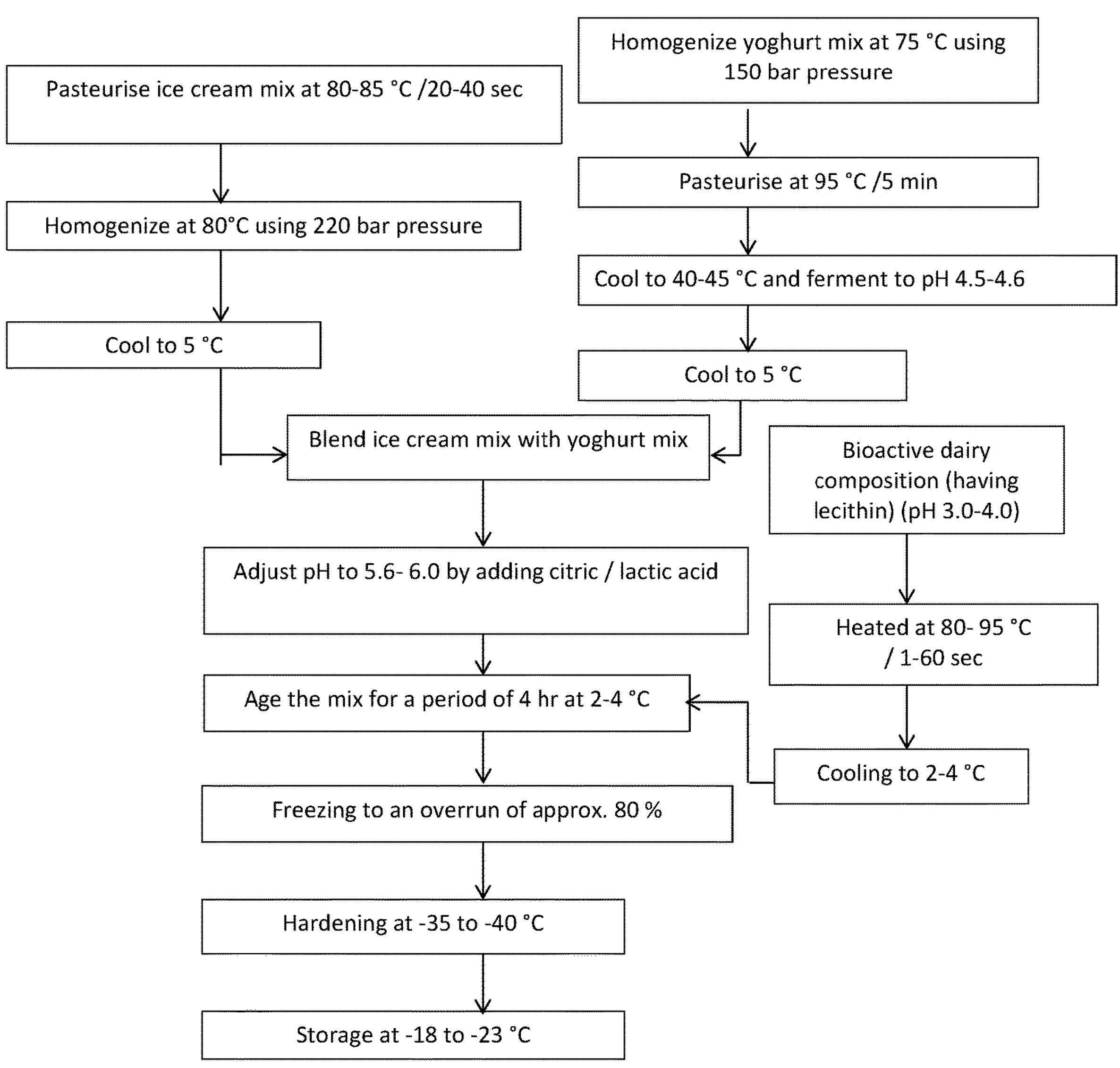
FIG. 9 shows a flow chart for producing a frozen yoghurt product containing active immunoglobulins in accordance with a further embodiment of the invention.

In frozen yoghurt the bioactive dairy composition is not added to the blend of ice cream and yoghurt mix as the ice cream mix and yoghurt mix are already pasteurised. Therefore, the bioactive dairy composition is pasteurised separately and added to the yoghurt mix-ice cream blend as shown in FIG. 9. If the bioactive dairy composition were added to the ice cream mix-yoghurt mix blend and the entire mix pasteurised, then this would result in "double pasteurisation" of the ice cream mix-yoghurt mix blend and unwanted possible interactions of IgG with the ice cream mix and yoghurt mix constituents resulting in much lower activity of IgG.

Figure 10:
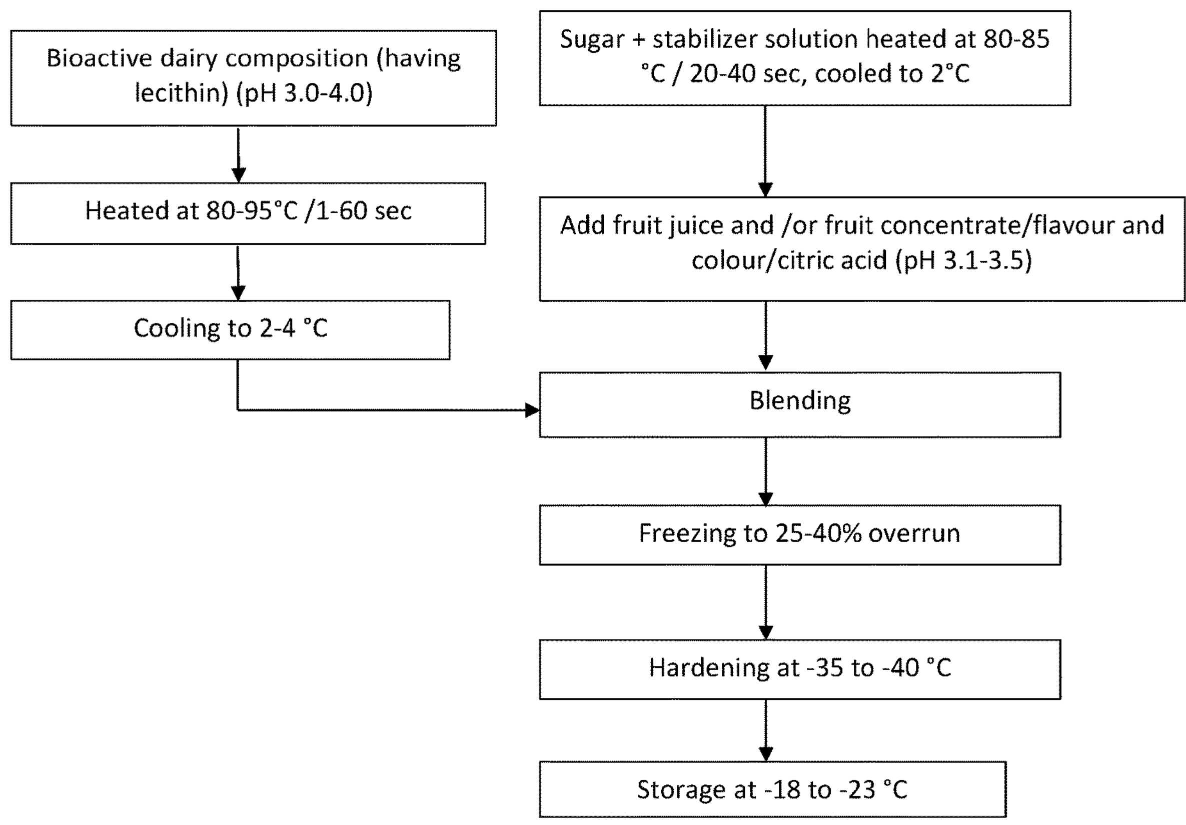
FIG. 10 shows a flow chart for producing a sorbet product containing active immunoglobulins in accordance with a further embodiment of the invention.
Figure 11:
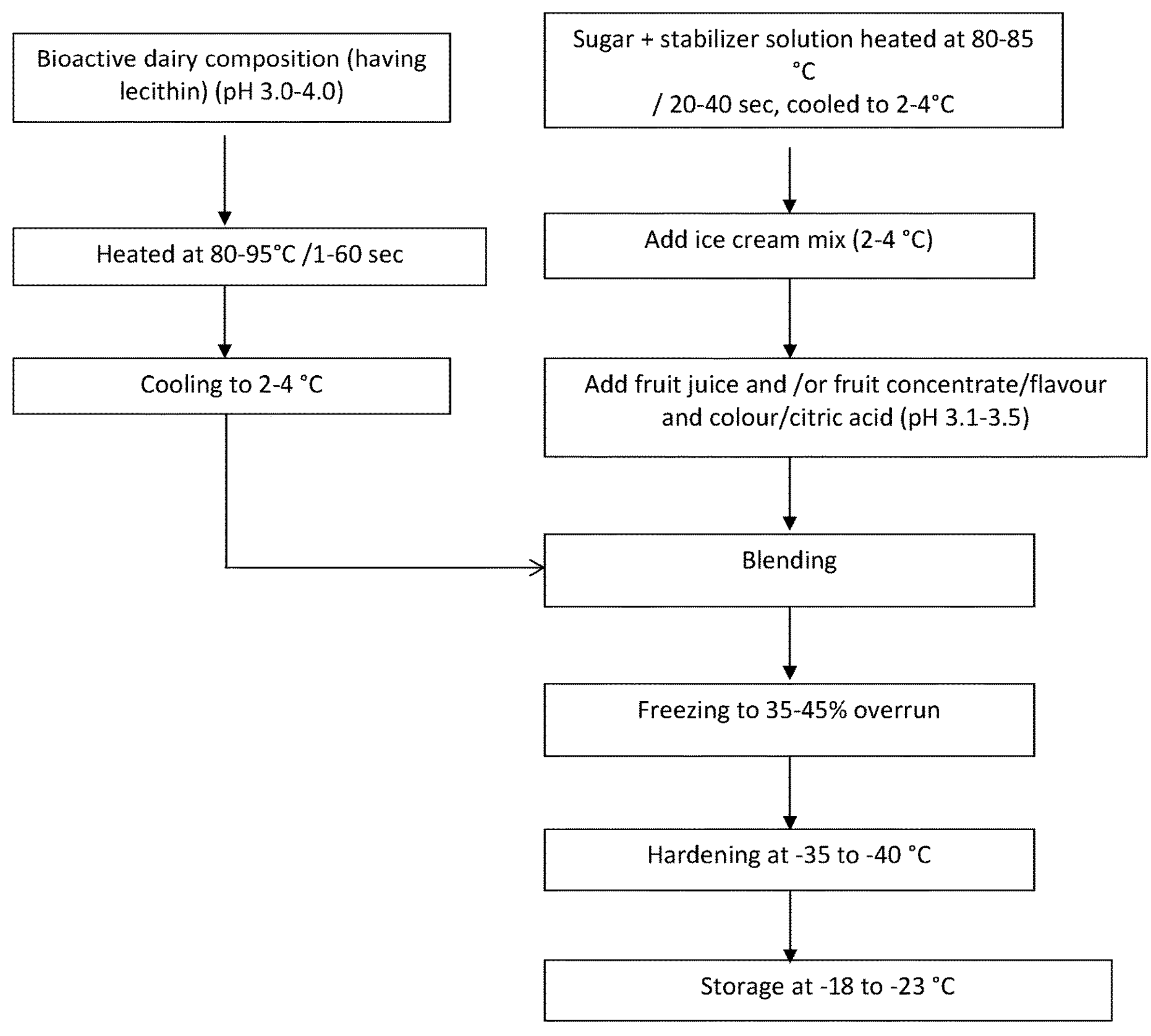
FIG. 11 shows a flow chart for producing a sherbet product containing active immunoglobulins in accordance with a further embodiment of the invention.

In the sorbet/sherbet making process also the bioactive dairy composition should be added separately as shown in FIG. 10 and FIG. 11, as direct addition of the bioactive dairy composition to the sugar and stabilizer solution (has high pH) and subsequent heating at 80-85° C./20-40 sec may result in much lower activity of IgG.

The amount of bioactive IgG retained after processing of different Ready to Drink (RTD) and Ready to Eat (RTE) products is influenced by the composition of the bioactive powder, amount of bioactive powder used for making a liquid bioactive composition, pH and heat treatment of the liquid bioactive composition, as demonstrated in the included examples. The applicant has developed a bioactive dairy composition having specific properties that enable the production of a wide range of dairy products having significantly higher levels of bioactive IgG than have previously been achievable using known techniques.

Table 10 below summarises the amount of retained active IgG present in a range of RTE and RTD products, the manufacturing processes exemplified in one embodiment of the invention above, utilising a bioactive dairy composition in the manufacturing process having a pH of 3.2-3.9.

TABLE 10

% Active IgG retained after processing of different products

| Type of product | % Retained Bioactive IgG in Final Product (using a bioactive dairy composition having pH range 3.2 -3.9) |
|---|---|
| Acidified beverages/ Acidified UHT beverages | 20-95% |
| Set Yoghurt/Stirred Yoghurt | 20-90% |
| UHT drinking Yoghurt | 20-90% |
| UHT Juice milk drink | 20-90% |
| Carbonated drink | 20-90% |
| Frozen yoghurt | 20-85% |
| Sorbet/Sherbet | 20-85% |

The bioactive dairy composition of the present invention may have a wide variety of uses. While its use in the preparation of food compositions is exemplified, the composition may also be included as an ingredient in pharmaceutical preparations, medicinal preparations or health supplements.

The entire disclosures of all applications, patents and publications cited above and below, if any, are herein incorporated by reference.

Reference to any prior art in this specification is not, and should not be taken as, an acknowledgement or any form of suggestion that prior art forms part of the common general knowledge in the field of endeavour in any country in the world.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

I claim:

1. A process for the preparation of a liquid or semi-liquid bioactive dairy composition containing 60-90% retained bioactive immunoglobulin G (IgG), for use as an ingredient in a ready-to-eat (RTE) or ready-to-drink (RTD) food product, the process including the steps of:

a) combining a bioactive powder containing a colostrum powder and/or milk powder containing whey proteins, and IgG, water and a food grade acid to form a bioactive dairy composition with a pH of 3.2-3.3; and b) wherein the process includes the further step of adding 0.12-0.31% w/w lecithin to the bioactive dairy composition and c) heat treating the bioactive dairy composition to between 86-92° C. at ambient pressure.

2. The process of claim 1, wherein step a) of the process further includes the steps of:

combining the bioactive powder containing a colostrum powder and/or milk powder containing whey proteins, and IgG, with a sweetening agent;

adding the bioactive powder and sweetening agent to water having a temperature of 20°-40° C. to form a mix and stirring;

following stirring, standardizing the mix to 1-43% w/w total solids with water;

ydrating the standardized mix for 25-35 minutes;

following hydration, cooling the mix to 2-25° C.; and acidifying the cooled mix by addition of a solution of food grade acid and stirring to achieve a pH of 3.2-3.3.

3. A process for the preparation of a ready-to-eat (RTE) or ready-to-drink (RTD) food product, the process including producing a bioactive dairy composition using the process of claim 1 and incorporating the bioactive dairy composition as an ingredient in the production of a (RTE) or ready-to-drink (RTD) food product.

4. A process for the preparation of a UHT RTD acidified beverage, the process including producing a bioactive dairy composition using the process of claim 1 and packing the product aseptically.

5. A process for the preparation of a ready-to-eat (RTE) or ready-to-drink (RTD) food product including a heat-treated liquid or semi-liquid bioactive dairy composition having a pH of 3.2-3.3, the process including:

a) combining a colostrum powder and/or milk powder, and immunoglobulin G (IgG), water and a food grade acid to form a bioactive dairy composition with a pH of 3.2-3.3; and b) wherein the process includes the further step of adding 0.12-0.31% w/w lecithin to the bioactive dairy composition; and c) heat treating the bioactive dairy composition to between at 86-92° C. at ambient pressure and d) incorporating the bioactive dairy composition into a food or beverage product to produce an RTE or RTD food product;

wherein the process provides an RTE or RTD food product including the bioactive dairy composition with a retained bioactive IgG level of 60-90%.

6. A process for the production of an RTD beverage selected from coffee, tea and hot chocolate, the process including the steps of incorporating a liquid or semi-liquid bioactive dairy composition formed using the process of claim 1 into a coffee, tea or hot chocolate beverage.

* * * * *